United States Patent
Podoll et al.

(10) Patent No.: US 10,858,364 B2
(45) Date of Patent: Dec. 8, 2020

(54) IMIDAZOPYRAZINE INHIBITORS OF BRUTON'S TYROSINE KINASE

(71) Applicant: Acerta Pharma B.V., Oss (NL)

(72) Inventors: Terry Podoll, Seattle, WA (US); Jerry Evarts, Seattle, WA (US); Allard Kaptein, Zalthommel (NL)

(73) Assignee: Acerta Pharma B.V., Oss (NL)

( * ) Notice: Subject to any disclaimer, the term of this patent is extended or adjusted under 35 U.S.C. 154(b) by 0 days.

(21) Appl. No.: 16/448,056

(22) PCT Filed: Dec. 21, 2017

(86) PCT No.: PCT/IB2017/058319
§ 371 (c)(1),
(2) Date: Jun. 21, 2019

(87) PCT Pub. No.: WO2018/116259
PCT Pub. Date: Jun. 28, 2018

(65) Prior Publication Data
US 2019/0345164 A1    Nov. 14, 2019

Related U.S. Application Data

(60) Provisional application No. 62/437,633, filed on Dec. 21, 2016, provisional application No. 62/569,028, filed on Oct. 6, 2017.

(51) Int. Cl.
*A61K 31/4985* (2006.01)
*A61P 35/00* (2006.01)
*C07D 487/04* (2006.01)

(52) U.S. Cl.
CPC .................... *C07D 487/04* (2013.01)

(58) Field of Classification Search
CPC .................................................. C07D 487/04
See application file for complete search history.

(56) References Cited

U.S. PATENT DOCUMENTS

2014/0155385 A1* 6/2014 Barf .................. A61K 31/55
514/217.05

FOREIGN PATENT DOCUMENTS

| EP | 2548877 A1 | 1/2013 |
|---|---|---|
| WO | 2008039218 A2 | 4/2008 |
| WO | 2013010869 A1 | 1/2013 |
| WO | 2015110923 A2 | 7/2015 |
| WO | 2016106627 A1 | 7/2016 |
| WO | 2016109223 A1 | 7/2016 |

OTHER PUBLICATIONS

Norman Expert Opinion on Investigational Drugs vol. 25 No. 8, pp. 891-899. (Year: 2016).*
International Search Report dated Feb. 20, 2018 for International Patent Application No. PCT/IB2017/058319, 7 pages.
Written Opinion dated Feb. 20, 2018 for International Patent Application No. PCT/IB2017/058319, 6 pages.
Translation of Eurasian Patent Office for Eurasian Patent Application No. 201991456, 2 pages.

* cited by examiner

*Primary Examiner* — Emily A Bernhardt
(74) *Attorney, Agent, or Firm* — Morgan, Lewis & Bockius LLP

(57) ABSTRACT

In some embodiments, the invention relates to the compounds of Formula (I) and (II) or a pharmaceutically acceptable salt thereof, or to pharmaceutical compositions comprising these compounds and to their use in therapy. In particular, in some embodiments, the present invention relates to the compounds of Formula (I) and (II), pharmaceutical compositions thereof, and the use of the compounds and pharmaceutical compositions in the treatment of a hyperproliferative disorder, an inflammatory disorder, an immune disorder, or an autoimmune disorder.

14 Claims, 13 Drawing Sheets

1. Oxidation
2. N-Dealkylation
3. Glutathione conjugation
4. Amide hydrolysis
5. Dehydration
6. Reduction
7. Hydration

IMIDAZOPYRAZINE INHIBITORS OF BRUTON'S TYROSINE KINASE

FIELD OF THE INVENTION

In some embodiments, the present invention relates to the compounds of Formula (I) and (II), to pharmaceutical compositions comprising these compounds, and to their use in therapy. In some embodiments, the present invention relates to the use of the compound of Formula (I) or (II) or a pharmaceutically acceptable salt in the treatment of a hyperproliferative disorder, an inflammatory disorder, an immune disorder, or an autoimmune disorder.

BACKGROUND OF THE INVENTION

Bruton's tyrosine kinase (BTK) is a Tec family non-receptor protein kinase expressed in B cells and myeloid cells. Research findings support a key role for BTK in the regulation of the production of auto-antibodies in autoimmune diseases. Also, inhibition of BTK seems to be relevant in particular for B cell lymphomas due to chronic active BCR signaling, as described in Davis, et al., Nature, 2010, 463, 88-94.

In many solid tumors, the supportive microenvironment (which may make up the majority of the tumor mass) is a dynamic force that enables tumor survival. The tumor microenvironment is generally defined as a complex mixture of "cells, soluble factors, signaling molecules, extracellular matrices, and mechanical cues that promote neoplastic transformation, support tumor growth and invasion, protect the tumor from host immunity, foster therapeutic resistance, and provide niches for dominant metastases to thrive," as described in Swartz, et al., Cancer Res., 2012, 72, 2473. Although tumors express antigens that should be recognized by T cells, tumor clearance by the immune system is rare because of immune suppression by the microenvironment. Addressing the tumor cells themselves with e.g. chemotherapy has also proven to be insufficient to overcome the protective effects of the microenvironment. New approaches are thus urgently needed for more effective treatment of solid tumors that take into account the role of the microenvironment.

SUMMARY OF THE INVENTION

In one aspect, the BTK inhibitor is a compound of Formula (I) having the structure:

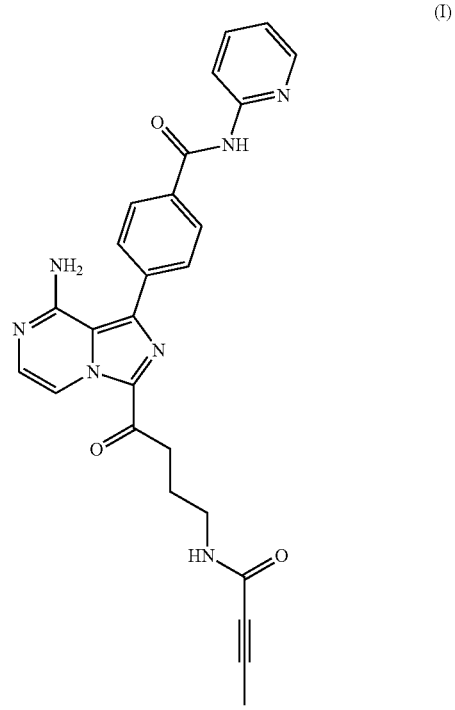 [SMILES: CC#CC(=O)NCCCC(=O)c1nc(-c2ccc(C(=O)Nc3ccccn3)cc2)c2c(N)nccn12]

(I)

or a pharmaceutically acceptable salt thereof.

In another aspect, the BTK inhibitor is a compound of Formula (II) having the structure:

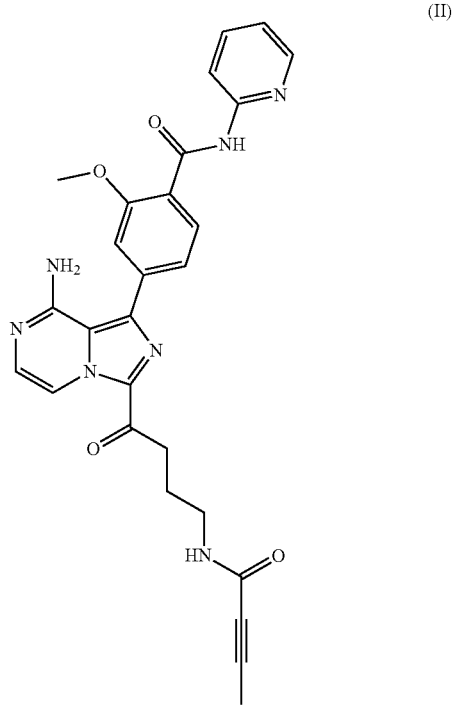 [SMILES: CC#CC(=O)NCCCC(=O)c1nc(-c2ccc(C(=O)Nc3ccccn3)c(OC)c2)c2c(N)nccn12]

(II)

or a pharmaceutically acceptable salt thereof.

In yet another aspect, the invention relates to the use of the compound of Formula (I) or (II) in the treatment of a hyperproliferative disorder, an inflammatory disorder, an immune disorder, or an autoimmune disorder.

BRIEF DESCRIPTION OF THE DRAWINGS

The foregoing summary, as well as the following detailed description of the invention, will be better understood when read in conjunction with the appended drawings.

DETAILED DESCRIPTION OF THE INVENTION

Figure 1:
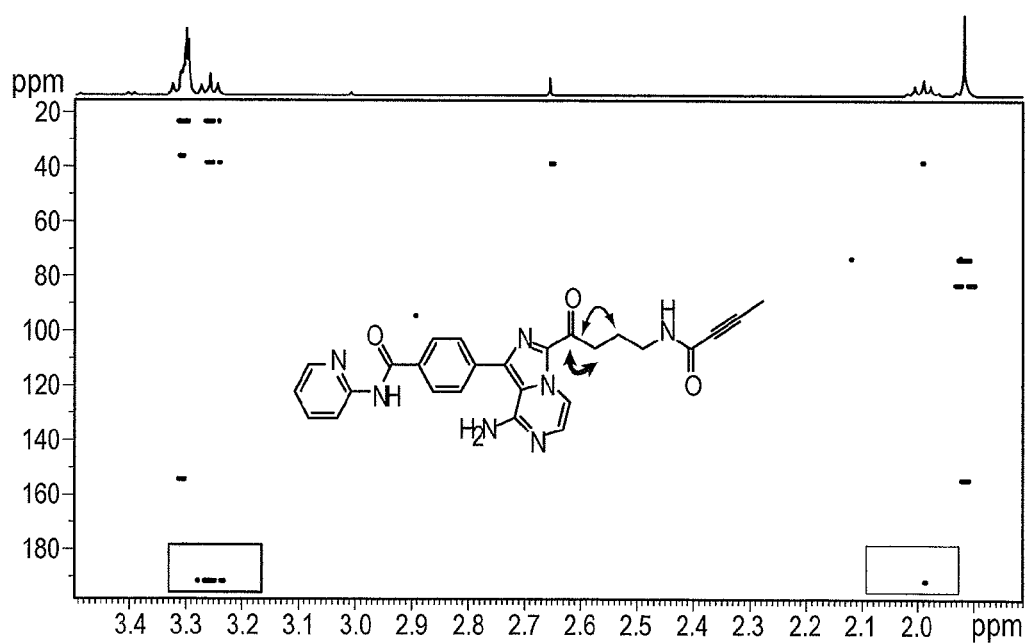
FIG. 1 illustrates $^1$H-$^{13}$C two/three-bond correlation NMR spectrum of the compound of Formula (I).

While preferred embodiments of the invention are shown and described herein, such embodiments are provided by way of example only and are not intended to otherwise limit the scope of the invention. Various alternatives to the described embodiments of the invention may be employed in practicing the invention.

Unless defined otherwise, all technical and scientific terms used herein have the same meaning as is commonly understood by one of skill in the art to which this invention belongs. All patents and publications referred to herein are incorporated by reference in their entireties.

The term "pharmaceutically acceptable salt" refers to salts derived from a variety of organic and inorganic counter ions known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In selected embodiments, the pharmaceutically acceptable base addition salt is chosen from ammonium, potassium, sodium, calcium, and magnesium salts.

"Pharmaceutically acceptable carrier" or "pharmaceutically acceptable excipient" is intended to include any and all solvents, dispersion media, coatings, antibacterial and antifungal agents, isotonic and absorption delaying agents. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the described compositions.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

Compounds

In a first embodiment there is provided a compound of Formula (I), also named as M27:

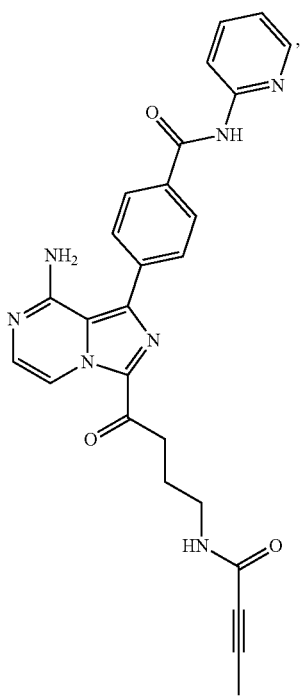

(I)

or a pharmaceutically acceptable salt thereof; or a compound of Formula (II):

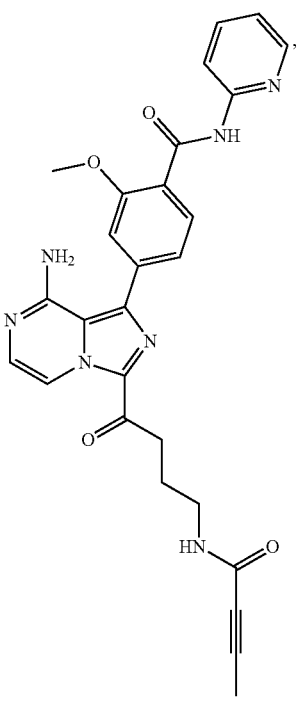

(II)

or a pharmaceutically acceptable salt thereof.

In one embodiment, the BTK inhibitor is a compound selected from the group consisting of: 4-(8-amino-3-(4-(but-2-ynamido)butanoyl)imidazo[1,5-a]pyrazin-1-yl)-N-(pyridin-2-yl)benzamide and 4-(8-amino-3-(4-(but-2-ynamido)butanoyl)imidazo[1,5-a]pyrazin-1-yl)-2-methoxy-N-(pyridin-2-yl)benzamide.

In one embodiment, the compound is a compound of Formula (I), or a pharmaceutically acceptable salt thereof.

In one embodiment, the compound is a compound of Formula (II), or a pharmaceutically acceptable salt thereof.

The compounds and salts of Formula (I) and (II) may exist in solvated forms and unsolvated forms. For example, a solvated form may be a hydrated form, such as a hemi-hydrate, a mono-hydrate, a di-hydrate, a tri-hydrate or an alternative quantity thereof.

The compounds and salts of Formula (I) and (II) likewise include crystalline and amorphous forms of the compounds of Formula (I) and (II), including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

In one embodiment there is provided a compound of Formula (I), or a pharmaceutically acceptable salt thereof, or a compound of Formula (II), or a pharmaceutically acceptable salt thereof, where the compound is in isolated form.

A compound of Formula (I), or a pharmaceutically acceptable salt thereof or Formula (II), or a pharmaceutically acceptable salt thereof in an "isolated form" is one which is substantially free of other components, for example organic components found in a living organism.

In one embodiment there is provided a compound of Formula (I), or a pharmaceutically acceptable salt thereof, or a compound of Formula (II), or a pharmaceutically acceptable salt thereof, where the compound is in a high purity of at least 90% pure measured by HPLC.

In one embodiment there is provided a compound of Formula (I), or a pharmaceutically acceptable salt thereof, or a compound of Formula (II), or a pharmaceutically acceptable salt thereof, where the compound is in a high purity of at least 95% pure measured by HPLC.

In one embodiment there is provided a compound of Formula (I), or a pharmaceutically acceptable salt thereof, or a compound of Formula (II), or a pharmaceutically acceptable salt thereof, where the compound is in a high purity of at least 96% pure measured by HPLC.

In one embodiment there is provided a compound of Formula (I), or a pharmaceutically acceptable salt thereof, or a compound of Formula (II), or a pharmaceutically acceptable salt thereof, where the compound is in a high purity of at least 97% pure measured by HPLC.

In one embodiment there is provided a compound of Formula (I), or a pharmaceutically acceptable salt thereof, or a compound of Formula (II), or a pharmaceutically acceptable salt thereof, where the compound is in a high purity of at least 98% pure measured by HPLC.

In one embodiment there is provided a compound of Formula (I), or a pharmaceutically acceptable salt thereof, or a compound of Formula (II), or a pharmaceutically acceptable salt thereof, where the compound is in a high purity of at least 99% pure measured by HPLC.

In one embodiment there is provided a compound of Formula (I), or a pharmaceutically acceptable salt thereof, or a compound of Formula (II), or a pharmaceutically acceptable salt thereof, where the compound is 100% pure measured by HPLC.

In one embodiment there is provided a compound of Formula (I), or a pharmaceutically acceptable salt thereof, or a compound of Formula (II), or a pharmaceutically acceptable salt thereof, where the compound has been produced ex-vivo.

"Ex-vivo" means outside a living organism, for example a human patient being treated for cancer or other disease.

In one embodiment there is provided a compound of Formula (I), or a pharmaceutically acceptable salt thereof, or a compound of Formula (II), or a pharmaceutically acceptable salt thereof, where the compound has been produced by organic synthesis. Organic synthetic routes are available for preparing the compound of Formula (I) or (II) or a pharmaceutically acceptable salt thereof in relative pure form, for example in purities of 80% or greater, 90% or greater, 95% or greater, 96% or greater, 97% or greater, 98% or greater, and 99% or greater measured by HPLC. Recrystallization and other purification methods can be carried out to provide compounds that are essentially 100% pure. Such synthetic methods and purification techniques are known in the art and are illustrated in non-limiting fashion in the Examples that follow.

"Organic synthesis" means the execution of synthetic reactions in a laboratory or manufacturing setting to obtain a product.

In one embodiment, the compound of Formula (I) or (II) or a pharmaceutically acceptable salt thereof are provided in substantially pure form. Substantially pure means that the compounds are pure enough for FDA approval and contain essentially no contaminants or other materials, or alternatively a level of impurity that does not adversely or unacceptably affect the properties of the compounds as regards safety, effectiveness, stability, and other desirable properties.

Pharmaceutical Compositions

In selected embodiments, the invention provides pharmaceutical compositions for treating solid tumor cancers, lymphomas and leukemia.

The pharmaceutical compositions are typically formulated to provide a therapeutically effective amount of the compound of Formula (I) or (II) as the active ingredients, or a pharmaceutically acceptable salt thereof. Where desired, the pharmaceutical compositions contain a pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

Where desired, other agent(s) may be mixed into a preparation or both components may be formulated into separate preparations for use in combination separately or at the same time.

In selected embodiments, the concentration of each of the compound of Formula (I) or (II) or a pharmaceutically acceptable salt provided in the pharmaceutical compositions of the invention is independently less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v, relative to the total mass or volume of the pharmaceutical composition.

In selected embodiments, the concentration of each of the compound of Formula (I) or (II) or a pharmaceutically acceptable salt provided in the pharmaceutical compositions of the invention is independently greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v, relative to the total mass or volume of the pharmaceutical composition.

In selected embodiments, the concentration of each of the compound of Formula (I) or (II) or a pharmaceutically acceptable salt of the invention is independently in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12% or approximately 1% to approximately 10% w/w, w/v or v/v, relative to the total mass or volume of the pharmaceutical composition.

In selected embodiments, the concentration of each of the compound of Formula (I) or (II) or a pharmaceutically acceptable salt of the invention is independently in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v, relative to the total mass or volume of the pharmaceutical composition.

In selected embodiments, the amount of each of the compound of Formula (I) or (II) or a pharmaceutically acceptable salt of the invention is independently equal to or less than 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g or 0.0001 g.

In selected embodiments, the amount of each of the compound of Formula (I) or (II) or a pharmaceutically acceptable salt of the invention is independently more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, or 3 g.

Each of the compound of Formula (I) or (II) or a pharmaceutically acceptable salt according to the invention is effective over a wide dosage range. For example, in the treatment of adult humans, dosages independently range from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician.

Described below are non-limiting pharmaceutical compositions and methods for preparing the same.

Dosages and Dosing Regimens

The amounts of the compound of Formula (I) or (II) or a pharmaceutically acceptable salt administered will be dependent on the mammal being treated, the severity of the disorder or condition, the rate of administration, the disposition of the compounds and the discretion of the prescribing physician. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day.

In selected embodiments, the compound of Formula (I) or (II) or a pharmaceutically acceptable salt is administered in a single dose. Typically, such administration will be by injection, for example by intravenous injection, in order to introduce the agents quickly. However, other routes may be used as appropriate. A single dose of the compound of Formula (I) or (II) or a pharmaceutically acceptable salt may also be used for treatment of an acute condition.

In selected embodiments, the compound of Formula (I) or (II) or a pharmaceutically acceptable salt is administered in multiple doses. Dosing may be about once, twice, three times, four times, five times, six times, or more than six times per day. Dosing may be about once a month, once every two weeks, once a week, or once every other day. In other embodiments, the compound of Formula (I) or (II) or a pharmaceutically acceptable salt is administered about once per day to about 6 times per day. In another embodiment the administration of the compound of Formula (I) or (II) continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In selected embodiments, the compound of Formula (I) or (II) or a pharmaceutically acceptable salt is administered for more than 1, 2, 3, 4, 5, 6, 7, 14, or 28 days. In some embodiments, the compound of Formula (I) or (II) or a pharmaceutically acceptable salt is administered for less than 28, 14, 7, 6, 5, 4, 3, 2, or 1 day. In selected embodiments, the compound of Formula (I) or (II) or a pharmaceutically acceptable salt is administered chronically on an ongoing basis—e.g., for the treatment of chronic effects.

An effective amount of the combination of the compound of Formula (I) or (II) or a pharmaceutically acceptable salt may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

Based on in vitro studies, acalabrutinib is predominantly metabolized by CYP3A enzymes, and to a lesser extent, by glutathione conjugation and amide hydrolysis. The compound of Formula (I) was identified as the major metabolite in plasma with a geometric mean exposure (AUC) approximately 2- to 3-fold higher than the exposure of acalabrutinib. The major metabolite is approximately 50% less potent than acalabrutinib with regard to BTK inhibition in a biochemical assay.

Acalabrutinib and the major metabolite form a covalent bond with a cysteine residue in the BTK active site, leading to inhibition of BTK enzymatic activity. Acalabrutinib binding with the cysteine residue occurs rapidly and irreversibly and provides high target occupancy at steady state. Based on clinical studies where subjects received a single oral dose of 100 mg acalabrutinib, the median terminal elimination half-life (t½) of acalabrutinib and the major metabolite were 0.9 (range: 0.6 to 2.8) hours and 6.9 hours, respectively. Acalabrutinib mean apparent oral clearance (CL/F) was 159 L/hr with similar pharmacokinetics between patients and healthy subjects based on population pharmacokinetics analysis.

It is possible that the more slowly cleared the major metabolite, which is available for a longer period of time as serum levels of the more rapidly cleared acalabrutinib decrease, provides additional benefit by inhibiting newly synthesized BTK enzyme and maintaining a higher level of effective BTK target occupancy over the dosing interval.

Acalabrutinib is a weak inhibitor of CYP3A4/5, CYP2C8 and CYP2C9, but does not inhibit CYP1A2, CYP2B6, CYP2C19, and CYP2D6. It is a weak inducer of CYP1A2, CYP2B6 and CYP3A4. The major metabolite is a weak inhibitor of CYP2C8, CYP2C9 and CYP2C19, but does not inhibit CYP1A2, CYP2B6, CYP2D6 and CYP3A4/5. It is a weak inducer of CYP3A4.

Methods of Treatment

In one embodiment, the invention relates to a method of treating a BTK-mediated disorder in a mammal that comprises administering to said mammal a therapeutically effective amount of the compound of Formula (I) or (II), or a pharmaceutically acceptable salt thereof.

In some embodiments, the invention relates to a method of treating a hyperproliferative disorder, an inflammatory disorder, an immune disorder, or autoimmune disorder in a mammal that comprises administering to said mammal a therapeutically effective amount of the compound of Formula (I) or (II), or a pharmaceutically acceptable salt thereof.

In some embodiments, the invention relates to a method of treating, with the compound of Formula (I) or (II) or a pharmaceutically acceptable salt, a hyperproliferative disorder in a mammal selected from the group consisting of bladder cancer, head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity and oropharyngeal cancers, gastric cancer, stomach cancer, cervical cancer, head, neck, renal cancer, kidney cancer, liver cancer, ovarian cancer, prostate cancer, colorectal cancer, esophageal cancer, testicular cancer, gynecological cancer, thyroid cancer, acquired immune deficiency syndrome (AIDS)-related cancers (e.g., lymphoma and Kaposi's sarcoma), viral-induced cancer, glioblastoma, esophogeal tumors, hematological neoplasms, primary central nervous system lymphoma, non-small-cell lung cancer (NSCLC), chronic myelocytic leukemia, diffuse large B-cell lymphoma (DLBCL), esophagus tumor, follicle center lymphoma, head and neck tumor, hepatitis C virus infection, hepatocellular carcinoma, Hodgkin's disease, metastatic colon cancer, multiple myeloma, non-Hodgkin's lymphoma, ovary tumor, pancreas tumor, renal cell carcinoma, small-cell lung cancer, or stage IV melanoma. In selected embodiments, the invention relates to a method of treating with a BTK inhibitor disorders such as hyperproliferative disorder, including but not limited to cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g., lymphoma and Kaposi's sarcoma) or viral-induced cancer. In some embodiments, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)). In particular embodiments, the method of treatment of the hyperproliferative disorder comprises administering to the mammal a compound of the invention (e.g. compound of Formula (I) or (II) or a pharmaceutically acceptable salt thereof). In one embodiment, the compound of Formula (I) or (II) or a pharmaceutically acceptable salt thereof is directly administered to the mammal, but is not concurrently administered to the mammal with another BTK inhibitor. In one embodiment, the compound of Formula (I) or (II) or a pharmaceutically acceptable salt thereof is directly administered to the mammal, but is not concurrently administered to the mammal with acalabrutinib. In one embodiment, the compound of Formula (I) or (II) or a pharmaceutically acceptable salt thereof is the sole BTK inhibitor directly administered to the mammal.

In some embodiments, the invention relates to a method of treating an inflammatory, immune, or autoimmune disorder in a mammal with the compound of Formula (I) or (II) or a pharmaceutically acceptable salt thereof. In particular embodiments the compound of Formula (I) or (II) or a pharmaceutically acceptable salt thereof is directly administered to the mammal. In one embodiment, the compound of Formula (I) or (II) or a pharmaceutically acceptable salt thereof is directly administered to the mammal, but is not concurrently administered to the mammal with another BTK inhibitor. In one embodiment, the compound of Formula (I) or (II) or a pharmaceutically acceptable salt thereof is directly administered to the mammal, but is not concurrently administered to the mammal with acalabrutinib. In one embodiment, the compound of Formula (I) or (II) or a pharmaceutically acceptable salt thereof is the sole BTK inhibitor directly administered to the mammal. In selected embodiments, the invention also relates to a method of treating a disease with the compound of Formula (I) or (II) or a pharmaceutically acceptable salt thereof, wherein the disease is selected from the group consisting of tumor angiogenesis, chronic inflammatory disease, rheumatoid arthritis, atherosclerosis, inflammatory bowel disease, skin diseases such as psoriasis, eczema, and scleroderma, Type 1 diabetes, Type 2 diabetes, diabetic retinopathy, retinopathy of prematurity, age-related macular degeneration, hemangioma, glioma and melanoma, ulcerative colitis, atopic dermatitis, pouchitis, spondylarthritis, uveitis, Behcets disease, polymyalgia rheumatica, giant-cell arteritis, sarcoidosis, Kawasaki disease, juvenile idiopathic arthritis, hidradenitis suppurativa, Sjögren's syndrome, psoriatic arthritis, juvenile rheumatoid arthritis, ankylosing spondylitis, Crohn's Disease, lupus, lupus nephritis, human leukocyte antigen (HLA) associated diseases, autoantibodies, immunotherapy, Addison's disease, autoimmune polyendocrine syndrome type 1 (APS-1), autoimmune polyendocrine syndrome type 2 (APS-2), Grave's disease, Hashimoto's thyroiditis, polyendocrine autoimmunity, iatrogenic autoimmunity, idiopathic hypoparathyroidism, vitilago, and lupus nephritis.

"Directly administering" means that the compound of Formula (I), or Formula (II) or a pharmaceutically acceptable salt of either thereof is dosed to the patient directly rather than being indirectly dosed by administration of a precursor molecule. For any embodiment where administering a compound of Formula (I), or Formula (II) or a pharmaceutically acceptable salt of either thereof to a warm blooded animal is mentioned in a general sense, a further embodiment is provided where said compound or salt is directly administered.

In some embodiments, the invention provides a method of treating an inflammatory, immune, or autoimmune disorder selected from the group consisting of rheumatoid arthritis (RA), juvenile RA, juvenile idiopathic arthritis, osteoarthritis, psoriatic arthritis, psoriasis vulgaris, pemphigus, bullous pemphigoid, osteoarthritis, infectious arthritis, progressive chronic arthritis, polymyalgia rheumatic, deforming arthritis, traumatic arthritis, gouty arthritis, Reiter's syndrome, polychrondritis, acute synovitis, ankylosing spondylitis, spondylitis, Sjogren's syndrome (SS), systemic lupus erythromatosus (SLE), discoid lupus erythromatosus (discoid LE), LE tumidus, lupus nephritis (LN), antiphospholipidosis, dermatomyositis, polymyositis, autoimmune hematologic disorders, thrombocytopenia, idiopathic thrombocytopenia purpura, thrombotic thrombocytopenia purpura, autoimmune (cold) agglutinin disease, autoimmune hemolytic anemia, cryoglobulinemia, aplastic anemia, neutropenia, autoimmune vasculitis, Behcet's disease, anti-neutrophil cytoplasmic antibody (ANCA)-associated vasculitis, scleroderma, systemic sclerosis, myasthenia gravis, multiple sclerosis (MS), chronic focal encephalitis, Guillian-Barre syndrome, chronic fatigue syndrome, systemic exertion intolerance disease, neuromyelitis optica, autoimmune uveitis, conjunctivitis, keratoconjuctivitis, Grave's disease, thyroid associated opthalmopathy, chronic thyroiditis, granulomatosis with microscopic polyangitis, Wegener's granulomatosis, autoimmune gastritis, autoimmune inflammatory bowel diseases, ulcerative colitis, Crohn's disease, graft versus host disease, idiopathic sprue, autoimmune hepatitis, active hepatitis (acute and chronic), idiopathic pulmonary fibrosis, bronchitis, pulmonary interstitial fibrosis, chronic inflammatory pulmonary disease, sarcoidosis, idiopathic membranous nephropathy, IgA nephropathy, glomerulosclerosis, glomerulonephritis (with or without nephrotic syndrome), pancreatitis and Type 1 or Type 2 diabetes.

In some embodiments, the invention provides a method of treating an inflammatory, immune, or autoimmune disorder selected from the group consisting of diabetic retinopathy, giant cell arteritis, Kawasaki disease, inflammatory bowel disease, irritable bowel disease, idiopathic sprue, enteropathy, post-herpetic neuralgia, polymyalgia rheumatic, primary biliary cirrhosis, myasthenia gravis, inflammatory pain, cachexia, periodontal disease, otitis media, pneumoconiosis, mononucleosis, pulmonary emphysema, pulmonary fibrosis, silicosis, chronic inflammatory pulmonary disease, chronic obstructive pulmonary disease, pulmonary insufficiency, pulmonary interstitial fibrosis, whipple, benign hyperplasia of the skin (e.g., psoriasis), myalgias caused by infections, cachexia secondary to infections, systemic exertion intolerance disease, atherosclerosis, granulomatosis, granulomatosis with microscopic polyangitis, hidradenitis suppurativa, age-related macular degeneration, and amyloidosis.

In some embodiments, the invention provides a method of treating an inflammatory, immune, or autoimmune disorder, wherein the inflammatory, immune, or autoimmune disorder is a dermatosis in which BTK-mediated signals are involved with the recruitment, activation and/or proliferation of inflammatory cells and production of inflammatory mediators and antimicrobial peptides in the skin. In some embodiments, the invention provides a method of treating a dermatosis wherein the dermatosis results from dermal manifestations of systemic diseases where sensitization, lymphocyte recruitment, lymphocyte skewing by local or lymph-node antigen presenting cells, activation of skin-resident or skin-homing lymphocytes, innate immune sensing, keratinocyte antimicrobial responses, activation of resident or infiltrating myeloid dendritic cells, plasmacytoid dendritic cells, macrophages, mast cells, neutrophils, and/or Langerhans cells leads to development of skin lesions. In some embodiments, the invention provides a method of treating a dermatosis selected from the group consisting of psoriasis vulgaris, guttate psoriasis, erythrodermic psoriasis, psoriatic nails, annular pustular psoriasis, pustular psoriasis, inverse psoriasis, psoriatic arthritis, keratoderma blennorrhagicum, parapsoriasis, erythema nodosum, palmoplantar hidradentitis, atopic dermatitis, atopic eczema, seborrheic eczema, seborrheic dermatitis, dyshidrosis, rosacea, cutaneous lupus erythematosus, acute cutaneous lupus erythematosus, subacute cutaneous lupus erythematosus, discoid lupus erythematosus, lupus erythromatosus tumidus, lupus nephritis (LN), lupus erythematosus panniculitis, erythema multiforme, verruca, verrucous lupus erythematosus, vitiligo, alopecia areata, purigo nodularis, lichen planus, purigo pigmentosum, pemphigus vulgaris, bullous pemphigoid, pemphigus erythematosus, pemphigus nodularis, erythrodermic sarcoidosis, granulomatous dermatisis, scleroderma, systemic sclerosis, cutaneous manifestations of systemic sclerosis, diffuse cutaneous mastocytosis, erythrodermic mastocytosis, granuloma annulare, chondrodermatitis nodularis, contact dermatitis, drug eruptions, linear IgA bullous dermatosis, eosinophilic dermatitis, keratosis pilaris, lymphomatoid papulosis, pityriasis lichenoides et varioliformis acuta (PLEVA), lichenoides chronica (PLC), febrile ulceronecrotic Mucha-Habermann disease (FUMHD), chronic urticaria, rheumatoid neutrophilic dermatitis, cryoglobulinemic purpura, and purpura hyperglobulinemica.

In some embodiments, the invention provides a method of treating a hyperproliferative disorder, wherein the hyperproliferative disorder is a chronic autoimmune and inflammatory disorder of the bone in which BTK signaling in osteoclasts, mast cells, and myeloid cells is involved in osteolysis, osteoclastic processes, imbalance of bone remodeling processes, or loss of bone density. Diseases of this nature, which often have an autoimmune component as well, include osteoarthritis, bone loss due to metastases, osteolytic lesions, osteoporosis, ankylosing spondylitis, spondylarthritis, diffuse idiopathic skeletal hyperostosis, gouty arthritis, and bone disorders related to multiple myeloma. In some embodiments, the invention provides a method of treating a hyperproliferative disorder, wherein the hyperproliferative disorder is selected from the group consisting of osteoarthritis, bone loss due to metastases, osteolytic lesions, osteoporosis, ankylosing spondylitis, spondylarthritis, diffuse idiopathic skeletal hyperostosis, gouty arthritis, and bone disorders related to multiple myeloma.

In some embodiments, the invention provides a method treating allergic and atopic diseases in which activated B cells produce IgE antibodies and mast cells degranulate following engagement of the FceR leading to release of pro-inflammatory factors and acute activation of local tissue responses as well as chronic changes to endothelial cells, neuroreceptors and other proximal structures which govern organ function. Such conditions include atopic dermatitis, contact dermatitis, eczema, atopic eczema, pemphigus vulgaris, bullous pemphigus, prurigo nodularis, Stevens-Johnson syndrome, asthma, airway hypersensitivity, bronchospasm, bronchitis, reactive asthma, chronic obstructive pulmonary disease, type 1 hypersensitivity, type 2 hypersensitivity, allergic rhinitis, allergic conjunctivitis, and other inflammatory or obstructive disease on airways. Allergies that can be treated or prevented include, among others, allergies to foods, food additives, insect poisons, dust mites, pollen, animal materials, metals, and certain drugs.

In an embodiment, the invention provides a method of treating graft-versus-host disease (GVHD), comprising the step of administering the compound of Formula (I) or (II) or a pharmaceutically acceptable salt thereof, wherein the GVHD is selected from the group consisting of GVHD associated with stem cell transplant, GVHD associated with bone marrow transplant, thymus GVHD, skin GVHD, gastrointestinal GVHD, liver GVHD, acute GVHD, and chronic GVHD. In particular embodiments, the compound of Formula (I) or (II) or a pharmaceutically acceptable salt thereof is directly administered to a mammal. In one embodiment, the compound of Formula (I) or (II) or a pharmaceutically acceptable salt thereof is directly administered to the mammal, but is not concurrently administered to the mammal with another BTK inhibitor. In one embodiment, the compound of Formula (I) or (II) or a pharmaceutically acceptable salt thereof is directly administered to the mammal, but is not concurrently administered to the mammal with acalabrutinib. In one embodiment, the compound of Formula (I) or (II) or a pharmaceutically acceptable salt thereof is the sole BTK inhibitor directly administered to the mammal.

In one embodiment, the medicament inhibits neurodegenerative diseases that involve the activation of microglia, recruitment and activation of macrophages, infiltration of inflammatory cells including myeloid cells that require BTK signaling to transmit activation signals, recognize integrins on activated endothelial cells, extravasate, or develop into cytokine and/or chemokine producing cells in situ. The inhibition of BTK by the compound of Formula (I) or (II) or a pharmaceutically acceptable salt thereof would inhibit disease activity or disease progression by inhibiting neurodegenerative diseases associated with the toxic aggregation of protein, such as accumulation of beta amyloid deposits (amyloid plaque), neurofibrillary tangles, tau aggregation and hyper-phosphorylation, intracytoplasmic inclusion bodies, intracytoplasmic paired helical filaments, polyglucosan inclusions, Papp-Lantos bodies, ubiquitin-containing inclusions, and disorders where inadequate control of protein degradation and/or inability to dispose of mis-folded proteins leads to neurodegeneration. Such diseases include sporadic and familial Alzheimer's disease, mild cognitive impairment, cerebral amyloid angiopathy, Lewy body dementia, Lewy body variant of Alzheimer's disease, Down's syndrome, Huntington's disease, striatonigral degeneration, multiple system atrophy (MSA-P, MSA-C, Shy-Drager syndrome), sporadic or hereditary amyotrophic lateral sclerosis (ALS or Lou Gehrig disease), primary lateral sclerosis, juvenile primary lateral sclerosis, neurodegenerative tauopathies, sporadic or hereditary synucleinopathies, neuronal intranuclear inclusion disease, Parkinson's disease, frontotemporal dementia with Parkinsonism linked to chromosome 17 (FTDP-17).

In an embodiment, the invention relates to a method of treating, with the compound of Formula (I) or (II) or a pharmaceutically acceptable salt thereof, a neurodegenerative disorder in a mammal wherein the inhibition of inflammatory processes in glial cells, myeloid cells, Schwann cells, oligodendrocytes and other myeloid-derived cell types resident in the CNS is accomplished through its covalent interaction with BTK and inhibition of signaling through the BTK pathway. Administration of the compound of Formula (I) or (II) or a pharmaceutically acceptable salt thereof would prevent or reduce neurodegeneration by inhibiting immune recognition and inflammatory responses toward misfolded and/or accumulated intracellular proteins due to trinucleotide repeat disorders (polyglutamine diseases), Huntington disease, spinocerebellar ataxia Types 1, 2, 3 (Machado-Joseph disease), 6, 7, and 17; spinal and bulbar muscular atrophy, Dentatorubral-pallidoluysian atrophy, neuronal ceroid lipofucsinoses, frontotemporal dementia (Pick's disease, primary progressive aphasia, and semantic dementia), corticobasal degeneration and progressive supranuclear palsy. In particular embodiments, the compound of Formula (I) or (II) or a pharmaceutically acceptable salt thereof is directly administered to a mammal. In one embodiment, the compound of Formula (I) or (II) or a pharmaceutically acceptable salt thereof is directly administered to the mammal, but is not concurrently administered to the mammal with another BTK inhibitor. In one embodiment, the compound of Formula (I) or (II) or a pharmaceutically acceptable salt thereof is directly administered to the mammal, but is not concurrently administered to the mammal with acalabrutinib. In one embodiment, the compound of Formula (I) or (II) or a pharmaceutically acceptable salt thereof is the sole BTK inhibitor directly administered to the mammal.

In another embodiment, administration of the compound of Formula (I) or (II) or a pharmaceutically acceptable salt thereof may be used to inhibit BTK in a mammal and thereby ameliorate inflammation-mediated neuronal death and other neuroinflammatory effects due to sporadic or hereditary prion disease, prion-disorders such as Creutzfeldt-Jakob disease, kuru, Gerstmann-Straussler-Scheinker syndrome, and disorders leading to olivopontocerebellar atrophy, sporadic fatal insomnia, fatal familial insomnia. In the case of familial prion disorders, administration of the compound of Formula (I) or (II) or a pharmaceutically acceptable salt thereof in a mammal may also be used to prevent and/or delay the occurrence of clinical manifestations of disease, in addition to reducing disease symptoms and slowing disease progression after the onset of clinical signs. In particular embodiments, the compound of Formula (I) or (II) or a pharmaceutically acceptable salt thereof is directly administered to a mammal. In one embodiment, the compound of Formula (I) or (II) or a pharmaceutically acceptable salt thereof is directly administered to the mammal, but is not concurrently administered to the mammal with another BTK inhibitor. In one embodiment, the compound of Formula (I) or (II) or a pharmaceutically acceptable salt thereof is directly administered to the mammal, but is not concurrently administered to the mammal with acalabrutinib. In one embodiment, the compound of Formula (I) or (II) or a pharmaceutically acceptable salt thereof is the sole BTK inhibitor directly administered to the mammal.

In an embodiment, the invention pertains to a method of treating, with the compound of Formula (I) or (II) or a pharmaceutically acceptable salt thereof, an autoimmune mediated neurodegenerative disorder in the central and/or peripheral nervous system. Through the inhibition of BTK mediated autoantibody production, the compound of Formula (I) or (II) or a pharmaceutically acceptable salt thereof may reduce the activation of myeloid derived cells resident in the tissues and inhibit transcytosis, extravasation and infiltration of circulating myeloid cells, thereby reducing inflammation. In addition, treatment with the compound of Formula (I) or (II) or a pharmaceutically acceptable salt thereof may reduce the activation of inflammatory processes at the endothelial-microglial interface and interstitial spaces, where lymphoid aggregates have been observed in autoimmune neuropathies, by 1) altering cross-talk between microglia and endothelial cells, 2) inhibiting the activation of B lymphocytes and their cognate antigen presentation to circulating or infiltrating T cells, and 3) reducing cytokine and/or chemokine production. These effects of BTK inhibition by covalent interaction with the compound of Formula (I) or (II) or a pharmaceutically acceptable salt thereof are thought to reduce infiltration of autoimmune T cells into grey matter and white matter, by inhibition of B cell activation, cytokine activation, and APC function, as well as by altering the development and maturation status of professional APCs including infiltrating monocytes, activated microglia, and oligodendrocytes. Thus, the method of treatment for autoimmunity-mediated neurodegenerative disorders with a covalent BTK inhibitor such as compounds of Formula (I) and (II) may impair disease progression by inhibiting innate immune processes as well as reducing antibody production and the activation of autoimmune T cells. The invention may slow the progression or induce remission of experimental autoimmune encephalopathy in animal models, and in human neuropathies including neuromyelitis optica (Devic's syndrome), Guillain-Barre syndrome, multiple sclerosis, clinically isolated syndrome, relapsing-remitting multiple sclerosis, malignant multiple sclerosis, primary progressive multiple sclerosis, neuromyelitis optica spectrum diseases, Balo concentric sclerosis, Marburg multiple sclerosis, diffuse myelinoclastic sclerosis, chronic focal encephalitis, Rasmussen's encephalitis, stiff person syndrome, myasthenia gravis, polyneuropathy associated with anti-MAG IgM monoclonal gammopathy. In particular embodiments, the compound of Formula (I) or (II) or a pharmaceutically acceptable salt thereof is directly administered to a mammal. In one embodiment, the compound of Formula (I) or (II) or a pharmaceutically acceptable salt thereof is directly administered to the mammal, but is not concurrently administered to the mammal with another BTK inhibitor. In one embodiment, the compound of Formula (I) or (II) or a pharmaceutically acceptable salt thereof is directly administered to the mammal, but is not concurrently administered to the mammal with acalabrutinib. In one embodiment, the compound of Formula (I) or (II) or a pharmaceutically acceptable salt thereof is the sole BTK inhibitor directly administered to the mammal.

In another embodiment, the invention relates to a method of treating, with the compound of Formula (I) or (II) or a pharmaceutically acceptable salt thereof, polyneuropathies resulting from infection or post-infection neuroinflammation in a mammal, including Bannworth syndrome (Lyme disease), chronic encephalomyelitis (Lyme disease); post-herpetic neuralgia; HTLV-1 associated myelopathy; progressive multifocal leukoencephalopathy; chronic fatigue syndrome (CFS), systemic exertion intolerance disease (SEID), myalgic encephalomyelitis (ME), post-viral fatigue syndrome (PVFS), chronic fatigue immune dysfunction syndrome (CFIDS); Meniere's disease (vertigo-inner ear endolymph fluid regulation), Guillain-Barre syndrome, amyotrophic lateral sclerosis, progressive bulbar palsy, infantile progressive bulbar palsy (or juvenile progressive bulbar palsy), Bell's palsy, vestibular neuritis, acute disseminated encephalomyelitis, recurrent or multiphasic disseminated encephalomyelitis, and chronic encephalomyelitis. In particular embodiments, the compound of Formula (I) or (II) or a pharmaceutically acceptable salt thereof is directly administered to a mammal. In one embodiment, the compound of Formula (I) or (II) or a pharmaceutically acceptable salt thereof is directly administered to the mammal, but is not concurrently administered to the mammal with another BTK inhibitor. In one embodiment, the compound of Formula (I) or (II) or a pharmaceutically acceptable salt thereof is directly administered to the mammal, but is not concurrently administered to the mammal with acalabrutinib. In one embodiment, the compound of Formula (I) or (II) or a pharmaceutically acceptable salt thereof is the sole BTK inhibitor directly administered to the mammal. In one embodiment, the mammal is a human.

In some embodiments, the hyperproliferative disorder is a solid tumor cancer selected from the group consisting of bladder cancer, squamous cell carcinoma, head and neck cancer, pancreatic ductal adenocarcinoma (PDA), pancreatic cancer, colon carcinoma, mammary carcinoma, breast cancer, fibrosarcoma, mesothelioma, renal cell carcinoma, lung carcinoma, thyoma, prostate cancer, colorectal cancer, ovarian cancer, acute myeloid leukemia, thymus cancer, brain cancer, squamous cell cancer, skin cancer, eye cancer, retinoblastoma, melanoma, intraocular melanoma, oral cavity cancer, oropharyngeal cancer, gastric cancer, stomach cancer, cervical cancer, renal cancer, kidney cancer, liver cancer, ovarian cancer, prostate cancer, colorectal cancer, esophageal cancer, testicular cancer, gynecological cancer, thyroid cancer, acquired immune deficiency syndrome (AIDS)-related cancers (e.g., lymphoma and Kaposi's sarcoma), viral-induced cancers such as cervical carcinoma (human papillomavirus), B-cell lymphoproliferative disease, nasopharyngeal carcinoma (Epstein-Barr virus), Kaposi's sarcoma and primary effusion lymphomas (Kaposi's sarcoma herpesvirus), hepatocellular carcinoma (hepatitis B and hepatitis C viruses), and T-cell leukemias (Human T-cell leukemia virus-1), glioblastoma, esophogeal tumors, head and neck tumor, metastatic colon cancer, head and neck squamous cell carcinoma, ovary tumor, pancreas tumor, renal cell carcinoma, hematological neoplasms, small-cell lung cancer, non-small-cell lung cancer, stage IV melanoma, and glioma.

In some embodiments, the hyperproliferative disorder is a B cell hematological malignancy selected from the group consisting of chronic lymphocytic leukemia (CLL), small lymphocytic leukemia (SLL), non-Hodgkin's lymphoma (NHL), diffuse large B cell lymphoma (DLBCL), follicular lymphoma (FL), mantle cell lymphoma (MCL), Hodgkin's lymphoma, B cell acute lymphoblastic leukemia (B-ALL), Burkitt's lymphoma, Waldenstrom's macroglobulinemia (WM), Burkitt's lymphoma, multiple myeloma, myelodysplastic syndromes, or myelofibrosis. In an embodiment, the invention relates to a method of treating a cancer in a mammal, wherein the cancer is chronic myelocytic leukemia, acute myeloid leukemia, DLBCL (including activated B-cell (ABC) and germinal center B-cell (GCB) subtypes), follicle center lymphoma, Hodgkin's disease, multiple myeloma, indolent non-Hodgkin's lymphoma, and mature B-cell ALL.

In some embodiments, the hyperproliferative disorder is a subtype of CLL. A number of subtypes of CLL have been characterized. CLL is often classified for immunoglobulin heavy-chain variable-region ($IgV_H$) mutational status in leukemic cells. R. N. Damle, et al., *Blood* 1999, 94, 1840-47; T. J. Hamblin, et al., *Blood* 1999, 94, 1848-54. Patients with $IgV_H$ mutations generally survive longer than patients without $IgV_H$ mutations. ZAP70 expression (positive or negative) is also used to characterize CLL. L. Z. Rassenti, et al., *N. Engl. J. Med.* 2004, 351, 893-901. The methylation of ZAP-70 at CpG3 is also used to characterize CLL, for example by pyrosequencing. R. Claus, et al., *J. Clin. Oncol.* 2012, 30, 2483-91; J. A. Woyach, et al., *Blood* 2014, 123, 1810-17. CLL is also classified by stage of disease under the Binet or Rai criteria. J. L. Binet, et al., *Cancer* 1977, 40, 855-64; K. R. Rai, T. Han, *Hematol. Oncol. Clin. North Am.* 1990, 4, 447-56. Other common mutations, such as 11q deletion, 13q deletion, and 17p deletion can be assessed using well-known techniques such as fluorescence in situ hybridization (FISH). In an embodiment, the invention relates to a method of treating a CLL in a human, wherein the CLL is selected from the group consisting of $IgV_H$ mutation negative CLL, ZAP-70 positive CLL, ZAP-70 methylated at CpG3 CLL, CD38 positive CLL, chronic lymphocytic leukemia characterized by a 17p13.1 (17p) deletion, and CLL characterized by a 11q22.3 (11q) deletion.

In some embodiments, the hyperproliferative disorder is a CLL wherein the CLL has undergone a Richter's transformation. Methods of assessing Richter's transformation, which is also known as Richter's syndrome, are described in P. Jain and S. O'Brien, *Oncology,* 2012, 26, 1146-52. Richter's transformation is a subtype of CLL that is observed in 5-10% of patients. It involves the development of aggressive lymphoma from CLL and has a generally poor prognosis.

In some embodiments, the hyperproliferative disorder is a CLL or SLL in a patient, wherein the patient is sensitive to lymphocytosis. In an embodiment, the invention relates to a method of treating CLL or SLL in a patient, wherein the patient exhibits lymphocytosis caused by a disorder selected from the group consisting of a viral infection, a bacterial infection, a protozoal infection, or a post-splenectomy state. In an embodiment, the viral infection in any of the foregoing embodiments is selected from the group consisting of infectious mononucleosis, hepatitis, and cytomegalovirus. In an embodiment, the bacterial infection in any of the foregoing embodiments is selected from the group consisting of pertussis, tuberculosis, and brucellosis.

In some embodiments, the hyperproliferative disorder is selected from the group consisting of myeloproliferative disorders (MPDs), myeloproliferative neoplasms, polycythemia vera (PV), essential thrombocythemia (ET), primary myelofibrosis (PMF), myelodysplastic syndrome, chronic myelogenous leukemia (BCR-ABL1-positive), chronic neutrophilic leukemia, chronic eosinophilic leukemia, or mastocytosis.

In one embodiment there is provided a compound of Formula (I), or a pharmaceutically acceptable salt thereof, or a compound of Formula (II), or a pharmaceutically acceptable salt thereof, for use in therapy.

In one embodiment there is provided the use of a compound of Formula (I), or a pharmaceutically acceptable salt thereof, or a compound of Formula (II), or a pharmaceutically acceptable salt thereof, in the manufacture of a medicament.

In one embodiment there is provided the use of a compound of Formula (I), or a pharmaceutically acceptable salt thereof, or a compound of Formula (II), or a pharmaceutically acceptable salt thereof, in the manufacture of a medicament, where the medicament is manufactured ex-vivo.

In any embodiment where the manufacture of a medicament is mentioned in a general sense, a further embodiment exists where the medicament is manufactured ex-vivo.

In one embodiment there is provided a compound of Formula (I), or a pharmaceutically acceptable salt thereof, or a compound of Formula (II), or a pharmaceutically acceptable salt thereof, for use in the treatment of a hyperproliferative disorder, an inflammatory disorder, an immune disorder, or autoimmune disorder in a mammal.

In one embodiment there is provided a compound of Formula (I), or a pharmaceutically acceptable salt thereof, for use in the treatment of a disease mediated by BTK, where the disease is a hyperproliferative disease. The hyperproliferative disease can be any hyperproliferative disease mentioned herein.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein. Reagents described in the examples are commercially available or may be prepared according to procedures described in the literature.

Example 1—Analytical Methods

The following liquid chromatography (LC) and mass spectrometry (MS) methods may be used to characterize compounds included in the present invention.

Method A
LC-MS spectrometer (Agilent)
Detector: DAD (210, 254 and 280 nm)
Mass detector: API-ES (10-2000 amu, pos./neg. ion mode)
Eluents (mobile phase): A: 0.1% formic acid in MilliQ-water, B: acetonitrile
Column: Waters XTerra C18 MS, 50×4.6 mm ID, 2.5 μm
Flow rate: 0.5 mL/min
Gradient elution program:

| Time (min) | A (%) | B (%) |
|---|---|---|
| 0.0 | 90 | 10 |
| 7.0 | 10 | 90 |
| 7.1 | 0 | 100 |
| 10.0 | 90 | 10 |

Method B:
HPLC: Gilson analytical HPLC system
Column: Phenomenex Luna C18(2) (100×2.00 mm, 5 μm)
Detector: UV/Vis (210/240 nm)
Flow rate: 1 mL/min
Eluents (mobile phase): A: acetonitrile, B: acetonitrile/MilliQ-water=1/9 (v/v), C: 0.1% TFA in MilliQ-water.
Gradient elution program:

| Time (min) | A (%) | B (%) | C (%) |
|---|---|---|---|
| 0.00 | 0 | 97 | 3 |
| 11.90 | 97 | 0 | 3 |
| 14.40 | 97 | 0 | 3 |
| 15.40 | 0 | 97 | 3 |

Example 2—Synthesis of the Compound of Formula (I)

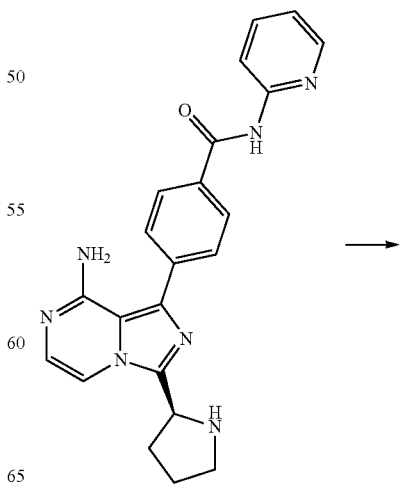

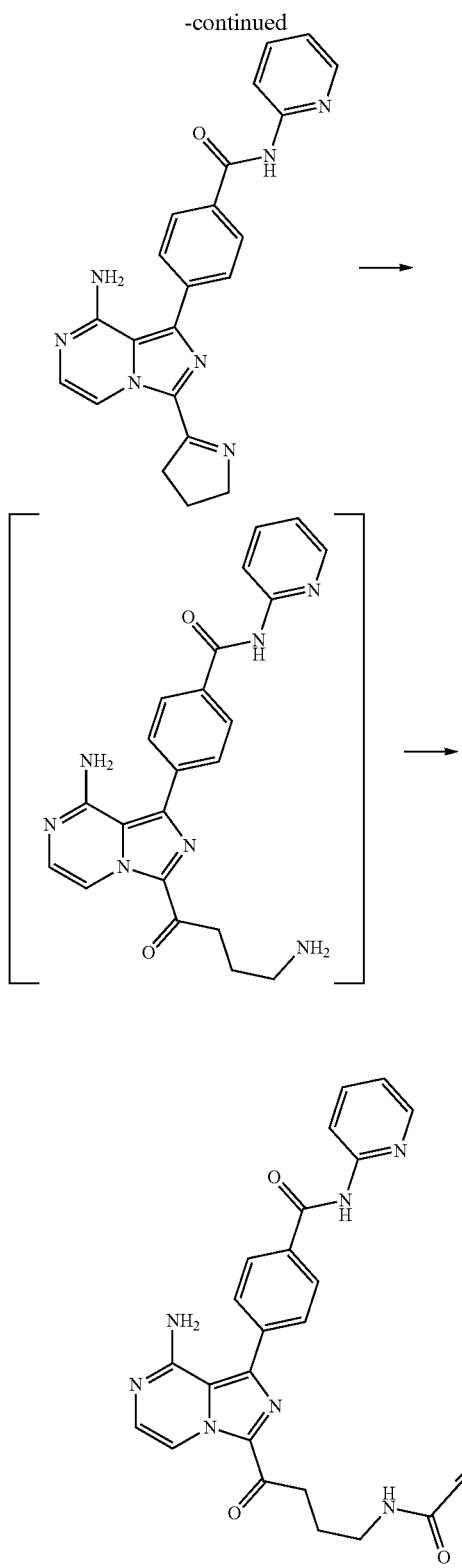

Preparation of 4-[8-amino-3-(pyrrolidin-2-yl)imidazo[1,5-a]pyrazin-1-yl]-N-pyridin-2-ylbenzamide This compound was essentially prepared according to the methods described in WO2013/010868.

Preparation of 4-[8-amino-3-(3,4-dihydro-2H-pyrrol-5-yl)imidazo[1,5-a]pyrazin-1-yl]-N-pyridin-2-ylbenzamide 4-[8-amino-3-[(2S)-pyrrolidin-2-yl]imidazo[1,5-a]pyrazin-1-yl]-N-(2-pyridyl)benzamide (1.13 g, 2.83 mmol) was suspended in DCM (50 mL). N-Chlorosuccinimide (416 mg, 3.11 mmol) was added and the mixture was stirred at 21° C. After 10 min, the reaction mixture was a clear pale yellow solution. Triethylamine (868 μL, 6.23 mmol) was added and the mixture continued stirring at 21° C. After 15 min of stirring, a white precipitate was formed. The precipitate was collected on a filter, washed with acetonitrile (20 mL) and air-dried. This yielded the title compound as a white solid (800 mg, 70%). MS (ESI+) m/z 398.2 (M+H)+; 1H NMR (400 Mhz, DMSO-d6, 300K): δ=7.72 (1H, d, J=5.0 Hz), 6.98 (1H, d, J=5.0 Hz), 4.45 (1H, t, J=6.9 Hz), 2.99 (1H, br s), 2.77-2.90 (2H, m), 2.09-2.20 (1H, m), 1.99-2.09 (1H, m), 1.78-1.89 (1H, m), 1.66-1.78 (1H, m).

Preparation of 4-(8-amino-3-(4-(but-2-ynamido)butanoyl)imidazo[1,5-a]pyrazin-1-yl)-N-(pyridin-2-yl)benzamide 4-[8-amino-3-(3,4-dihydro-2H-pyrrol-5-yl)imidazo[1,5-a]pyrazin-1-yl]-N-(2-pyridyl)benzamide (167 mg, 1.69 mmol) was dispersed in methanol (26.8 mL). Whilst stirring, concentrated hydrochloric acid (12 M, 670 μL, 8.04 mmol) was added. After 30 min, a white precipitate formed. All solvent was evaporated, rinsed with toluene (10 mL) and evaporated again. The resulting white solid was dispersed in acetone (70 mL), and triethylamine (705 μL, 5.06 mmol) was added. A solution of butyonyl chloride (207.4 mg, 2.02 mmol) in acetone (2 mL) was added dropwise, and the white solid gradually dissolved. The volatiles were removed in vacuo and the residue taken up in chloroform (200 mL), washed with water (200 mL) and brine. The aqueous phases were extracted with chloroform (2×50 mL). The combined organic layers were washed with brine, dried over sodium sulfate, filtered and concentrated by rotary evaporation yielding 657 mg of a pale yellow solid. The crude product was purified using chromatography on silica gel (90 g) eluting with 2-5% MeOH (containing 10% ammonium hydroxide) in DCM. The pure product fractions were pooled and concentrated in vacuo, yielding 228 mg (27%) of a pale yellow solid. LC-MS (Method A) Rt: 3.76 min; m/z 482.1 (M+H)+; HPLC (Method B) Rt: 5.79 min; purity 99.8%; 1H NMR (400 Mhz, DMSO-d6, 300K): δ=10.91 (1H, s), 8.72 (1H, d, J=4.8 Hz), 8.54 (1H, t, J=6.0 Hz), 8.42 (1H, d, J=4.9 Hz), 8.22 (3H, t, J=8.5 Hz), 7.87 (1H, dt, J1=1.9 Hz), 7.82 (2H, d, J=8.5 Hz), 7.51 (1H, d, J=4.8 Hz), 7.19 (1H, dd, J1=0.9 Hz, J2=4.8 Hz), 6.47 (2H, s), 3.11-3.26 (4H, m), 1.93 (3H, s), 1.83 (2H, m).

Example 3—Synthesis of the Compound of Formula (II)

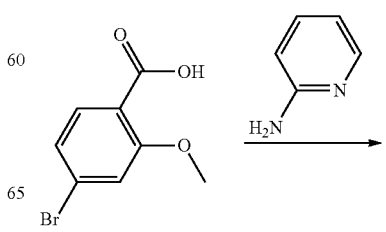

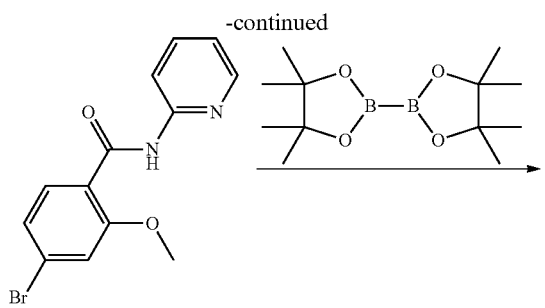

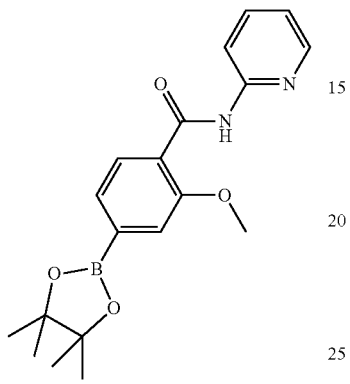

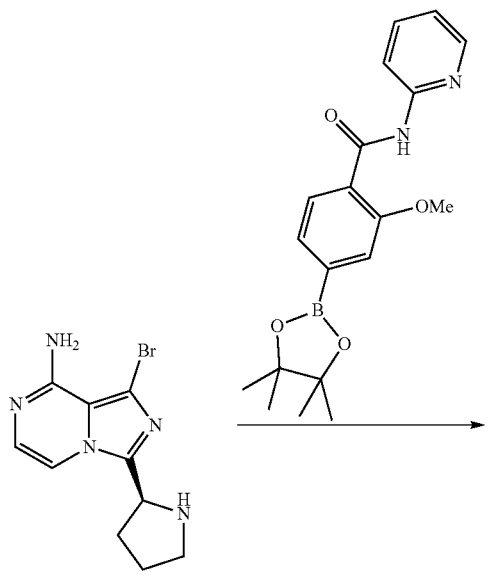

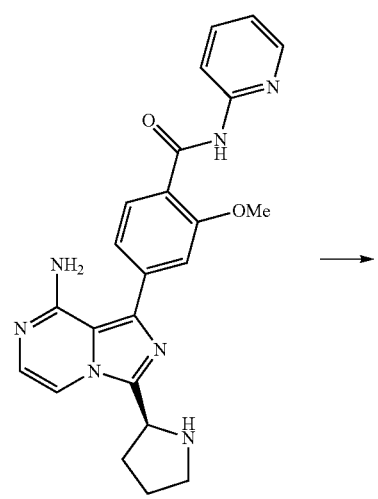

To a solution of 4-bromo-2-methoxy-benzoic acid (15.3 g, 66.2 mmol) in dichloromethane (250 mL) was added pyridin-2-amine (6.9 g, 72.8 mmol) and DIPEA (34.6 mL, 198.7 mmol). HATU (32.7 g, 86.1 mmol) was added and the mixture was stirred at room temperature overnight. Water (200 mL) was added and the reaction mixture was stirred for 1 hour. The organic layer was concentrated under reduced pressure. DCM (50 mL) was added and the solution was allowed to crystallize over the weekend. The solids were filtered off, washed twice with diethyl ether (10 mL) and dried under reduced pressure to give 4-bromo-2-methoxy-N-(2-pyridyl)benzamide (14.4 g, 66.8%) as light brown crystals. LC-MS (Method A) Rt: 6.05 min; m/z 307.0+309.0 (1:1) (M+H)$^+$.

To a solution of 4-bromo-2-methoxy-N-(2-pyridyl)benzamide (14.4 g, 46.9 mmol) in 1,4-dioxane (175 mL) was added bis(pinacolata)diboron (14.3 g, 56.3 mmol) and potassium acetate (9.2 g, 93.8 mmol). PdCl2(dppf).DCM (1.9 g, 2.3 mmol) was added and the mixture was stirred at 100° C. for 5 hours. The reaction mixture was diluted with water (150 mL) and extracted twice with ethyl acetate (150 mL). The combined organic layers were dried over sodium sulfate, filtered and concentrated under reduced pressure. The residue was purified by flash column chromatography (0 to 50% ethyl acetate in heptane). The fractions containing product were concentrated under reduced pressure. The residue was suspended in heptane (150 mL) and stirred for 30 minutes. The solids were filtered off and washed twice with heptane (15 mL), to give 2-methoxy-N-(2-pyridyl)-4-(4,4,5,5-tetramethyl-1,3,2-dioxaborolan-2-yl)benzamide (10.4 g, 62.6%) as a white solid. LC-MS (Method A) Rt: 6.86 min; m/z 355.2 (M+H)$^+$. 1H NMR (400 MHz, DMSO-d6, 300 K): δ=10.51 (1H, s), 8.36 (1H, m), 8.26 (1H, d, J=8.4 Hz), 7.89 (1H, d, J=7.6 Hz), 7.85 (1H, m), 7.41 (1H, dd, J1=7.6 Hz, J2=0.9 Hz), 7.38 (1H, s), 7.17 (1H, m), 4.01 (3H, s), 1.33 (12H, s).

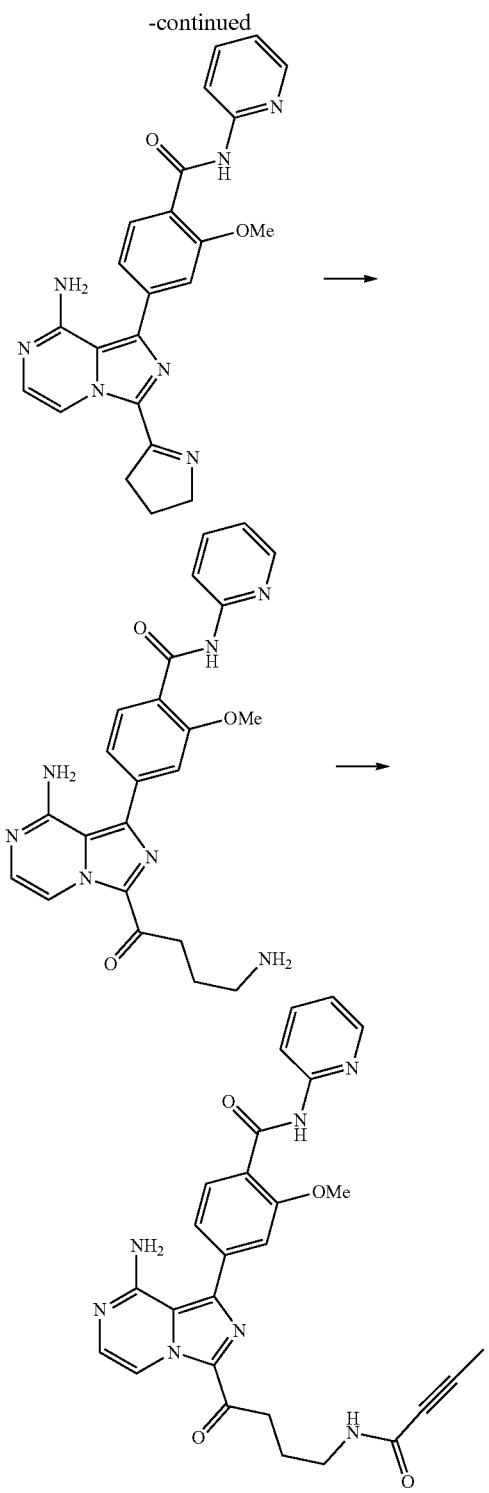

Preparation of 1-Bromo-3-[(2S)-pyrrolidin-2-yl]imidazo[1,5-a]pyrazin-8-amine

A 2000 mL round bottom flask equipped with a magnetical stirrer was charged with 37% hydrogen chloride (660 mL, 7971 mmol). Benzyl (2S)-2-(8-amino-1-bromo-imidazo[1,5-a]pyrazin-3-yl)pyrrolidine-1-carboxylate sulfuric acid (205 g, 399 mmol) was added portion wise (appr. 30 min) and the reaction mixture was stirred for 8 hours at 50° C. The reaction mixture was allowed to cool to room temperature over 8 h. The reaction mixture was washed with MTBE (3×1200 mL). 33% sodium hydroxide in water (~600 mL) was added drop-wise to the aqueous phase until a pH of appr. 14 was reached, while maintaining the temperature at 20-30° C. (MTBE layer appears). After addition, the aqueous phase was stirred for 1 hr, and extracted with dichloromethane (2×1500 mL). Activated carbon (10 g) was added to the combined DCM layers and the mixture was stirred for 1 hr at 40° C. The solids were removed by filtration over dicalite and the filtrate was concentrated under reduced pressure to give 1-bromo-3-[(2S)-pyrrolidin-2-yl]imidazo[1,5-a]pyrazin-8-amine (112.3 g, 397.9 mmol, 99.8% yield) as an off-white solid. LC-MS (Method A) Rt: 0.673 min; m/z 282.0+284.0 (1:1) (M+H)$^+$; 1H NMR (400 Mhz, DMSO-d6, 300K): δ=7.72 (1H, d, J=5.0 Hz), 6.98 (1H, d, J=5.0 Hz), 4.45 (1H, t, J=6.9 Hz), 2.99 (1H, br s), 2.77-2.90 (2H, m), 2.09-2.20 (1H, m), 1.99-2.09 (1H, m), 1.78-1.89 (1H, m), 1.66-1.78 (1H, m).

Preparation of 4-[8-amino-3-[(2S)-pyrrolidin-2-yl]imidazo[1,5-a]pyrazin-1-yl]-2-methoxy-N-(2-pyridyl)benzamide 1-Bromo-3-[(2S)-pyrrolidin-2-yl]imidazo[1,5-a]pyrazin-8-amine (112.3 g, 398.03 mmol), 2-methoxy-N-(2-pyridyl)-4-(4,4,5,5-tetramethyl-1,3,2-dioxaborolan-2-yl)benzamide (148.04 g, 417.93 mmol) and potassium iodide (19.82 g, 119.41 mmol) were loaded into a three-necked 3 L flask. 2-Butanol (550 mL) and water (880 mL) were added and the resulting suspension was stirred while nitrogen gas was bubbled through. Triethyl amine (165.97 mL, 1194.1 mmol) was added, and the suspension slowly dissolved. Bis(tert-butyldicylcohexylphosphine)dichloro palladium(II) (Pd-166, 1.37 g, 1.99 mmol) was added and the reaction mixture was deoxygenated again during 10 minutes and stirred at 82° C. overnight to give a tan-colored suspension. The reaction mixture was allowed to cool to room temperature. The mixture was then heated to 40° C. and water (1800 mL) was added, and after the addition allowed to cool to room temperature again. The mixture was filtered and the cake was washed with water (500 mL) and heptane (300 mL). The solid was suspended in heptane (500 mL) and co-evaporated. The solid was co-evaporated again with heptane (500 ml) and dried under reduced pressure at 50° C. overnight to give 4-[8-amino-3-[(2S)-pyrrolidin-2-yl]imidazo[1,5-a]pyrazin-1-yl]-2-methoxy-N-(2-pyridyl)benzamide (142.11 g, 330.9 mmol, 83.1% yield) as a light yellow solid. LC-MS (Method A) Rt: 2.885 min; m/z 430.1 (M+H)$^+$; HPLC (Method B) Rt: 1.483 min; purity 98.1%; 1H NMR (400 Mhz, DMSO-d6, 300K): δ=10.49 (1H, s), 8.37 (1H, m), 8.30 (1H, d, J=8.3 Hz), 8.04 (1H, d, J=8.0 Hz), 7.87 (1H, dt, J1=1.9 Hz, J2=7.8 Hz), 7.79 (1H, d, J=5.0 Hz), 7.43 (1H, s), 7.39 (1H, dd, J1=1.4 Hz, J2=8.0 Hz), 7.18 (1H, dd, J1=1.0 Hz, J2=8.0 HzHz), 7.09 (1H, d, J=4.9 Hz), 6.20 (2H, s), 4.55 (1H, t, J=7.5 Hz), 4.07 (3H, s), 2.90 (2H, t, J=7.2 Hz), 2.25 (1H, m), 2.12 (1H, m), 1.89 (1H, m), 1.78 (1H, m).

Preparation of 4-[8-amino-3-(3,4-dihydro-2H-pyrrol-5-yl)imidazo[1,5-a]pyrazin-1-yl]-2-methoxy-N-(2-pyridyl)benzamide 4-[8-amino-3-[(2S)-pyrrolidin-2-yl]imidazo[1,5-a]pyrazin-1-yl]-2-methoxy-N-(2-pyridyl)benzamide (250 mg, 0.58 mmol) was brought and partly dissolved in DCM (20 mL). N-Chlorosuccinimide (85.1 mg, 0.64 mmol) was added and the mixture was stirred at 21° C. After 10 min the reaction mixture was a clear yellow solution. Triethylamine (177.1 µL, 1.27 mmol) was added and the mixture continued stirring at 21° C. After 30 min of stirring a precipitate was formed. The precipitate was isolated using a centrifuge, yielding the title compound as an off-white solid (187.7 mg, 75.8%). HPLC (chloro intermediate) (Method B) Rt: 5.596 min.

Preparation of 4-[8-amino-3-(4-aminobutanoyl)imidazo[1,5-a]pyrazin-1-yl]-2-methoxy-N-(2-pyridyl) benzamide Trihydrochloride 4-[8-amino-3-(3,4-dihydro-2H-pyrrol-5-yl)imidazo[1,5-a]pyrazin-1-yl]-2-methoxy-N-(2-pyridyl)benzamide (187.7 mg, 0.44 mmol) was taken-up in methanol (8 mL). Concentrated hydrochloric acid (174.5 µL, 2.09 mmol) was added. The mixture was stirred for 1.5h. The solid was obtained by filtration, yielding the title compound as a light yellow solid in a quantitative yield (269 mg). HPLC (Method B) Rt: 3.790 min.

Preparation of 4-(8-amino-3-(4-(but-2-ynamido) butanoyl)imidazo[1,5-a]pyrazin-1-yl)-2-methoxy-N-(pyridin-2-yl)benzamide 4-[8-amino-3-(4-aminobutanoyl)imidazo[1,5-a]pyrazin-1-yl]-2-methoxy-N-(2-pyridyl)benzamide trihydrochloride (250 mg, 0.451 mmol) was suspended in DCM (14 mL) with acetone (2 mL). HATU (289.7 mg, 0.762 mmol), triethylamine (254.7 µL, 1.833 mmol) and 2-butynoic acid (64.1 mg, 0.762 mmol) were added. The mixture was stirred overnight at 21° C. The reaction mixture was concentrated in vacuo. The crude product was purified using flash chromatography (0-7% methanol in DCM). The product fractions were combined and concentrated in vacuo. The residue was suspended in methanol (2 mL) and the solvent was removed using a centrifuge. The solids were washed with diethylether (2 mL) and dried in vacuo yielding the title compound as an off-white solid (76.2 mg, 33.1%). LC-MS (Method A) Rt: 4.300 min; m/z 512.2 (M+H)$^+$; HPLC (Method B) Rt: 6.499 min; purity 98.8%; 1H NMR (400 Mhz, DMSO-d6, 300K): δ=10.51 (1H, s), 8.73 (1H, d, J=4.8 Hz), 8.55 (1H, t, J=6.3 Hz), 8.38 (1H, m), 8.30 (1H, d, J=8.5 Hz), 8.06 (1H, d, J=7.9 Hz), 7.88 (1H, dt, J1=1.9 Hz, J2=4.3 Hz), 7.52 (1H, d, J=4.8 Hz), 7.50 (1H, d, J=1.3 Hz), 7.44 (1H, dd, J1=1.5 Hz, J2=8.0 Hz), 7.19 (1H, m), 6.55 (2H, s), 4.08 (3H, s), 3.20 (2H, t, J=7.2 Hz), 3.16 (2H, q, J=6.0 Hz), 1.93 (3H, s), 1.83 (2H, t, J=7.9 Hz).

Example 4—Measurement of Kinase Activity of BTK and Other Kinases with Cysteine in Same Position as Cys481 in BTK

TABLE 1

| Kinase | Method | Formula I IC$_{50}$ (nM) | Formula II IC$_{50}$ (nM) |
| --- | --- | --- | --- |
| BTK | IMAP | 5.0 ± 1.0 | 9.3 |
| TEC | LanthaScreen | 345 ± 34 | |
| ITK | IMAP | >10,000 | >10,000 |
| TXK | Z'-LYTE | 567 ± 174 | 59 |
| BMX | Z'-LYTE | 15 ± 2 | |
| EGFFR | Z'-LYTE | >10,000 | |
| ERBB2 | Z'-LYTE | 552 ± 166 | |
| ERBB4 | Z'-LYTE | 343 ± 23 | |
| BLK | Z'-LYTE | 6170 ± 3348 | |
| JAK3 | Z'-LYTE | >10,000 | |

BTK enzyme activity is measured using the IMAP (immobilized metal ion affinity-based fluorescence polarization) assay as outlined below.

BTK enzyme (His-BTK (Millipore catalog #14-552)), is diluted to 0.4 U/mL in KR buffer (10 mM Tris-HCl, 10 mM MgCl$_2$, 0.01% Tween-20, 0.05% NaN$_3$, 1 mM DTT, 2 mM MnCl$_2$, pH 7.2).

Serial dilutions log 10 from 2 mM to 63.2 nM of test compounds are made in 100% DMSO. The dilutions in DMSO are then diluted 50-fold in KR-buffer. Final compound concentration range in the assay ranged from 10 µM to 0.316 nM.

The assay is performed as follows: 5 µL/well of test compound in KR buffer (final DMSO concentration in the assay is 1%) is mixed with 5 l/well of 0.4 U/mL BTK enzyme (final concentration in the assay is 0.1 U/mL). Test compounds and BTK enzyme are pre-incubated 60 minutes at room temperature, before adding 5 µL/well of 200 nM Fluorescin labeled substrate peptide (Blk/Lyntide substrate, e.g. # R7188/# R7233, Molecular Devices) in KR-buffer. Final peptide substrate concentration in assay is 50 nM. The kinase assay is started by adding 5 µL/well of 20 µM ATP in KR-buffer (final ATP concentration is 5 µM ATP, Km ATP in BTK IMAP assay). Following incubation for 2 hours at room temperature the enzyme reaction is stopped by adding 40 µL/well IMAP Progressive Binding Solution (according to suppliers (Molecular Devices) protocol using 75% 1× buffer A and 25% 1× buffer B with 1:600 Progressive Binding Solution). After 60 min incubation at room temperature in the dark the FP signal is read. Fluorescence at 535 nm is measured using parallel and perpendicular filters to determine differences in rotation due to binding of the phosphorylated substrate peptide to the beads. Values are calculated as percentage of the difference in readout (AmPi) of the controls with and without ATP. IC$_{50}$ values are determined by curve fitting of the experimental results in Dotmatics. The results are reported in Table 1.

ITK enzyme activity is measured using the IMAP (immobilized metal ion affinity-based fluorescence polarization) assay as outlined below.

ITK enzyme (Millipore #14-660M) is diluted to 0.2 U/mL in KR buffer (10 mM Tris-HCl, 10 mM MgCl$_2$, 0.01% Tween-20, 0.1% NaN$_3$, 1 mM DTT, 2 mM MnCl$_2$, pH 7.5)

Serial dilutions log 10 from 2 mM to 63.2 nM of test compounds are made in 100% DMSO. The dilutions in DMSO are then diluted 50-fold in KR-buffer. Final compound concentration range in the assay ranged from 10 µM to 0.316 nM.

The assay is performed as follows: 5 µL/well of test compound in KR buffer (final DMSO concentration in the assay is 1%) is mixed with 5 µL/well of 0.2 U/mL ITK enzyme (final concentration in the assay is 0.05 U/mL (8.4 nM)). Test compounds and ITK enzyme are pre-incubated 60 minutes at room temperature, before adding 5 µL/well of 200 nM Fluorescin labeled substrate peptide (Blk/Lyntide substrate # R8124, Molecular Devices) in KR-buffer. Final peptide substrate concentration in assay is 50 nM. The kinase assay is started by adding 5 µL/well of 20 µM ATP in KR-buffer (final ATP concentration is 5 µM ATP, Km ATP in ITK IMAP assay). Following incubation for 2 hours at room temperature the enzyme reaction is stopped by adding 40 µL/well IMAP Progressive Binding Solution (according to suppliers (Molecular Devices) protocol using 60% 1× buffer A and 40% 1× buffer B with 800× diluted beads (Progressive Binding System, Molecular Devices # R8124). After 60 min incubation at room temperature in the dark the FP signal is read. Fluorescence at 535 nm is measured using parallel and perpendicular filters to determine differences in rotation due to binding of the phosphorylated substrate peptide to the beads. Values are calculated as percentage of the difference in readout (AmPi) of the controls with and without ATP. $IC_{50}$ values are determined by curve fitting of the experimental results in Dotmatics.

TEC enzyme activity is measured using the LanthaScreen assay from ThermoFisher as outlined below.

TEC enzyme (LifeTech # PV3269) and Eu-anti-HIS antibody (Invitrogen # PV5596) are mixed and diluted in kinase buffer (50 mM Hepes pH 7.5+10 mM MgCl2+1 mM EGTA+0.01% Brij-35) to 3 and 6 nM, respectively. Final concentration in the assay for enzyme and antibody are 1 and 2 nM, respectively.

Tracer (Kinase Tracer 178, Invitrogen # PV5593) is diluted in Kinase buffer to 3 nM. Final concentration in the assay is 1 nM.

Serial dilutions log 10 from 1 mM to 3.16 nM of test compounds are made in 100% DMSO. The dilutions in DMSO are then diluted 33-fold in Kinase buffer (50 mM Hepes pH 7.5+10 mM MgCl2+1 mM EGTA+0.01% Brij-35).

The assay is performed as follows: 5 µL/well of TEC enzyme and EU-anti-His antibody dilution is mixed with 5 µL/well tracer dilution and 5 µL/well of compound dilution in Kinase buffer. Final compound concentration in the assay ranged from 10 µM to 0.316 nM, with 1% DMSO final concentration in assay. Following a 2h incubation at room the TR-FRET signal at 615 nm and 665 nm is read. The ratio 665/615 was used to calculate values expressed as percentage of the difference in readout (S/N) of the controls with and without Tracer. IC50 values were determined by curve fitting of the experimental results in Dotmatics.

BMX, TXK, EGFR, ERBB2, ERBB4, JAK3, BLK kinase activity was measured using the Z'-LYTE assay at Thermo Fisher. A 10-point dose response (final concentration in assay ranged from 10 µM to 0.5 nM in 3-fold dilution per dilution step) was generated with 1 h incubation of the test compound with the kinase prior to initiation of the kinase reaction by the addition of ATP. ATP concentration in the assay was Km ATP for the different kinases. IC50 values are determined by curve fitting of the experimental results at Thermo Fisher.

Example 5—BTK IMAP with ATP Competition to Investigate Covalent Binding of Compounds BTK enzyme activity with ATP competition was measured using the IMAP (immobilized metal ion affinity-based fluorescence polarization) assay.

BTK enzyme (Millipore) was diluted to 16 nM, respectively in Kinase Reaction (KR) buffer (10 mM Tris-HCl, 10 mM MgCl2, 0.01% Tween-20, 0.1% NaN3, 1 mM DTT, 2 mM MnCl2, pH 7.5).

Serial dilutions log 100 from 1 mM to 31.6 nM of test compounds were made in 100% DMSO. The dilutions in DMSO were then diluted 25-fold in KR-buffer. Final compound concentrations ranged from 10 µM to 0.316 nM.

The assay is performed as follows: 5 µL/well of test compound in KR buffer (final DMSO concentration in the assay is 1%) was mixed with 5 l/well of BTK or ITK enzyme (final concentration in the assay was 4 and 8 nM for BTK and ITK, respectively). Test compounds and kinase enzyme were pre-incubated 0, 30, or 60 min, before adding 5 µL/well of 200 nM Fluorescein labeled substrate peptide (Blk/Lyntide substrate, Molecular Devices) in KR-buffer. Final peptide substrate concentration in assay was 50 nM. The kinase assay was started by adding 5 µL/well of 20, 100, or 400 µM ATP in KR-buffer (final ATP concentration was 5, 25, or 100 µM ATP). Following incubation for 2h at room temperature the enzyme reaction was stopped by adding 40 µL/well IMAP Progressive Binding Solution (Molecular Devices), according to product instructions, using 60% lx buffer A and 40% lx buffer B with 800× diluted beads). After 60 min incubation at room temperature in the dark the FP signal was read. Fluorescence at 535 nm was measured using parallel and perpendicular filters to determine differences in rotation due to binding of the phosphorylated substrate peptide to the beads. Values were calculated as percentage of the difference in readout (AmPi) of the controls with and without ATP. IC50 values were determined by curve fitting of the experimental results using Dotmatics.

Figure 2:
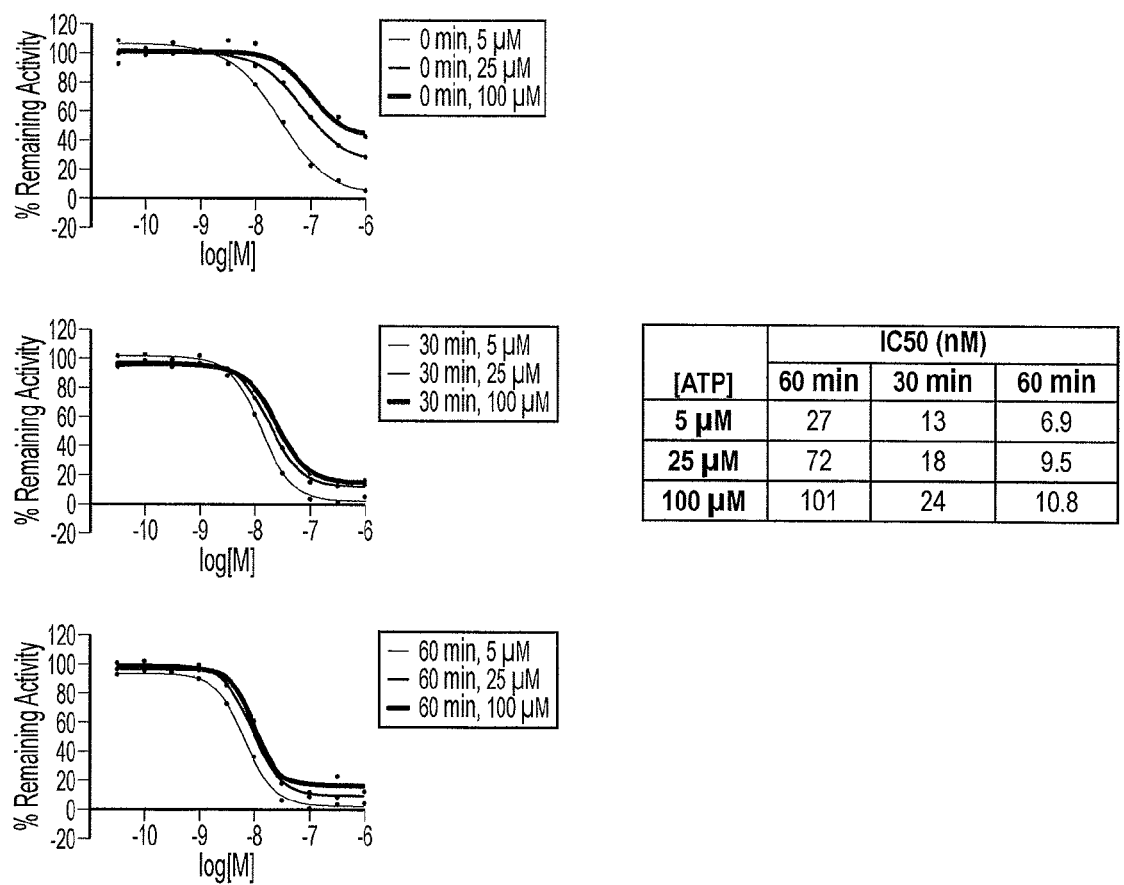
FIG. 2 illustrates the activities of the compound of Formula (I) with variation of pre-incubation time (0, 30, or 60 min) and ATP concentration (5, 25, or 100 µM) in the BTK IMAP assay.
Figure 3:
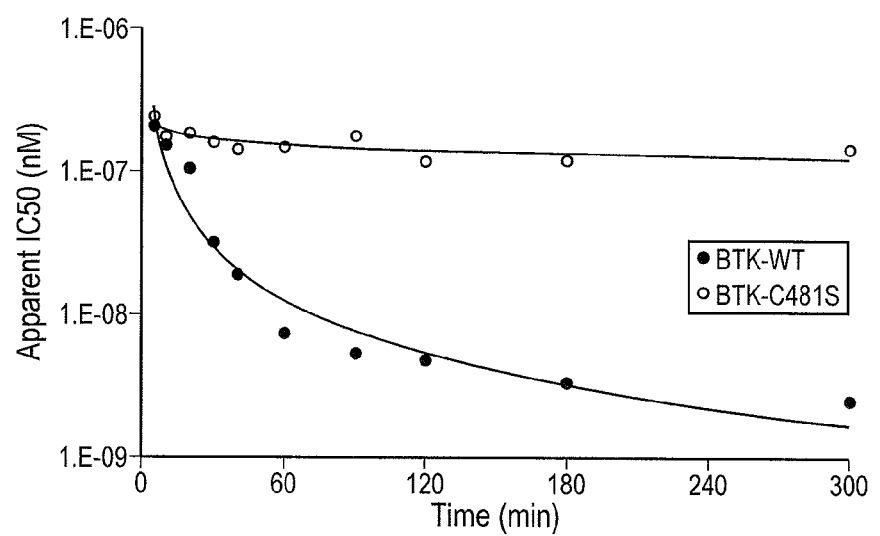
FIG. 3 illustrates the apparent IC50 of the compound of Formula (I) over time on BTK wild type (BTK-WT) and the BTK mutant Cys481Ser (BTK-C481S) using the LanthaScreen assay.
Figure 4:
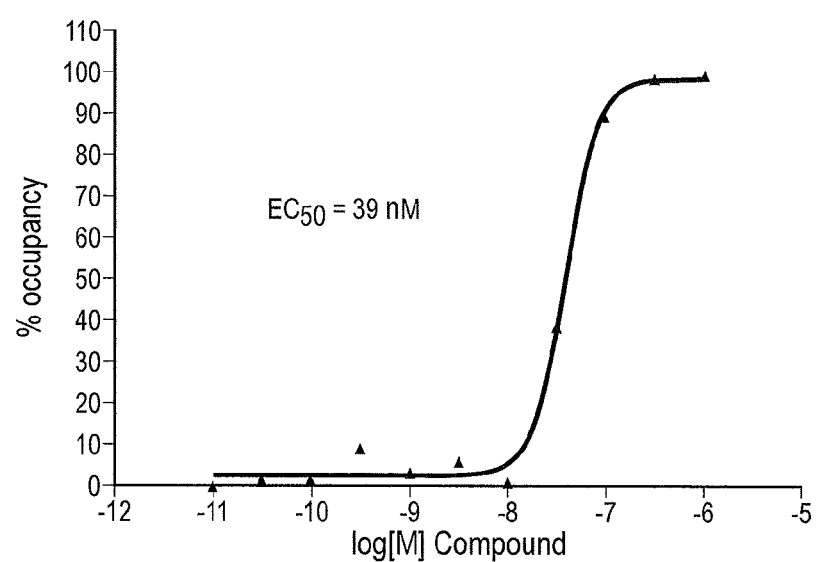
FIG. 4 illustrates the dose response of the compound of Formula (I) on BTK target occupancy in Ramos B cells.
Figure 5:
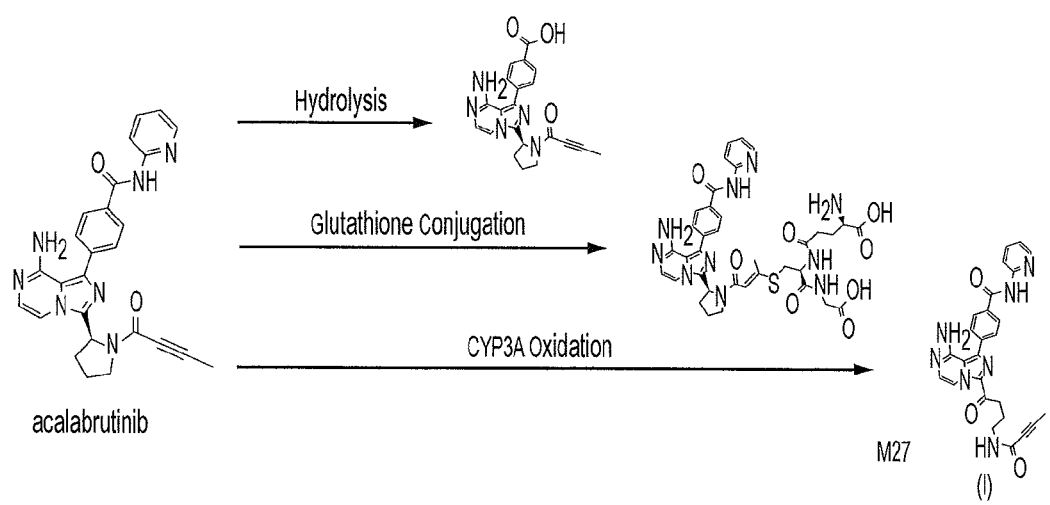
FIG. 5 illustrates the primary metabolic routes of acalabrutinib.
Figure 6:
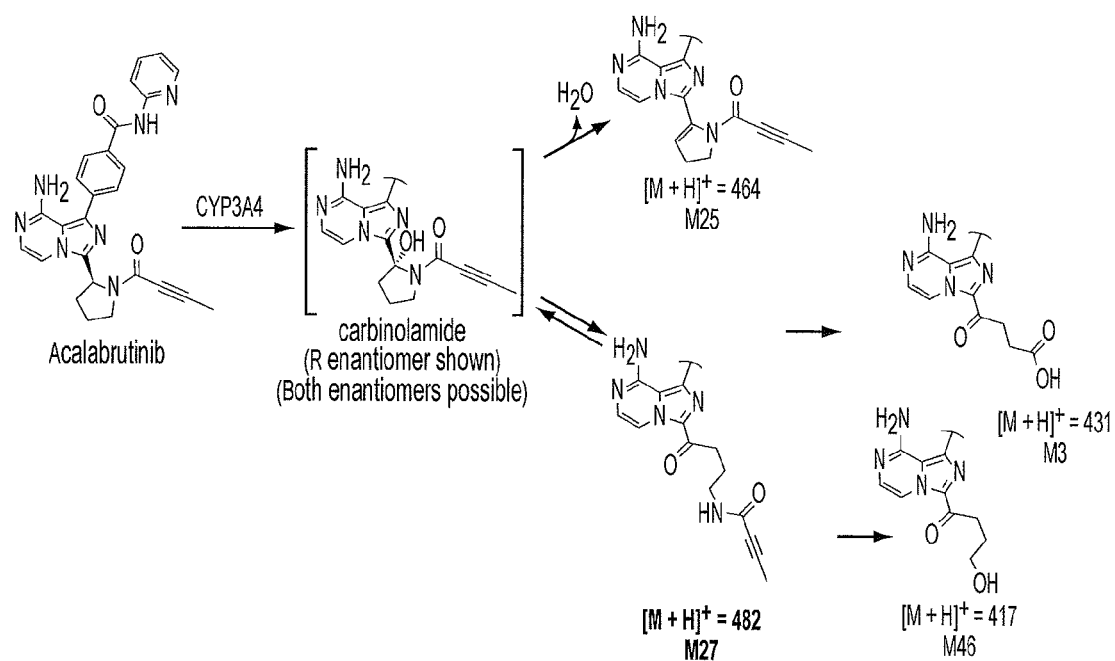
FIG. 6 illustrates the major oxidation metabolic pathway to M27 from acalabrutinib.
Figure 7:
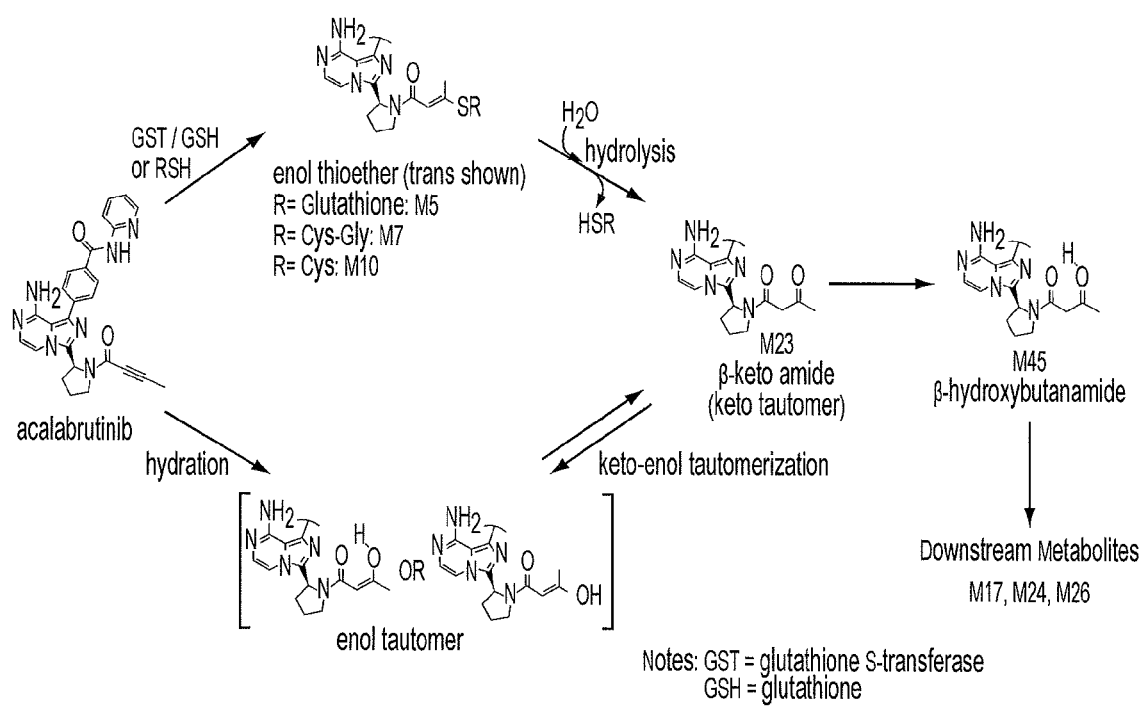
FIG. 7 illustrates the metabolic pathways to M23 from acalabrutinib.
Figure 8A:
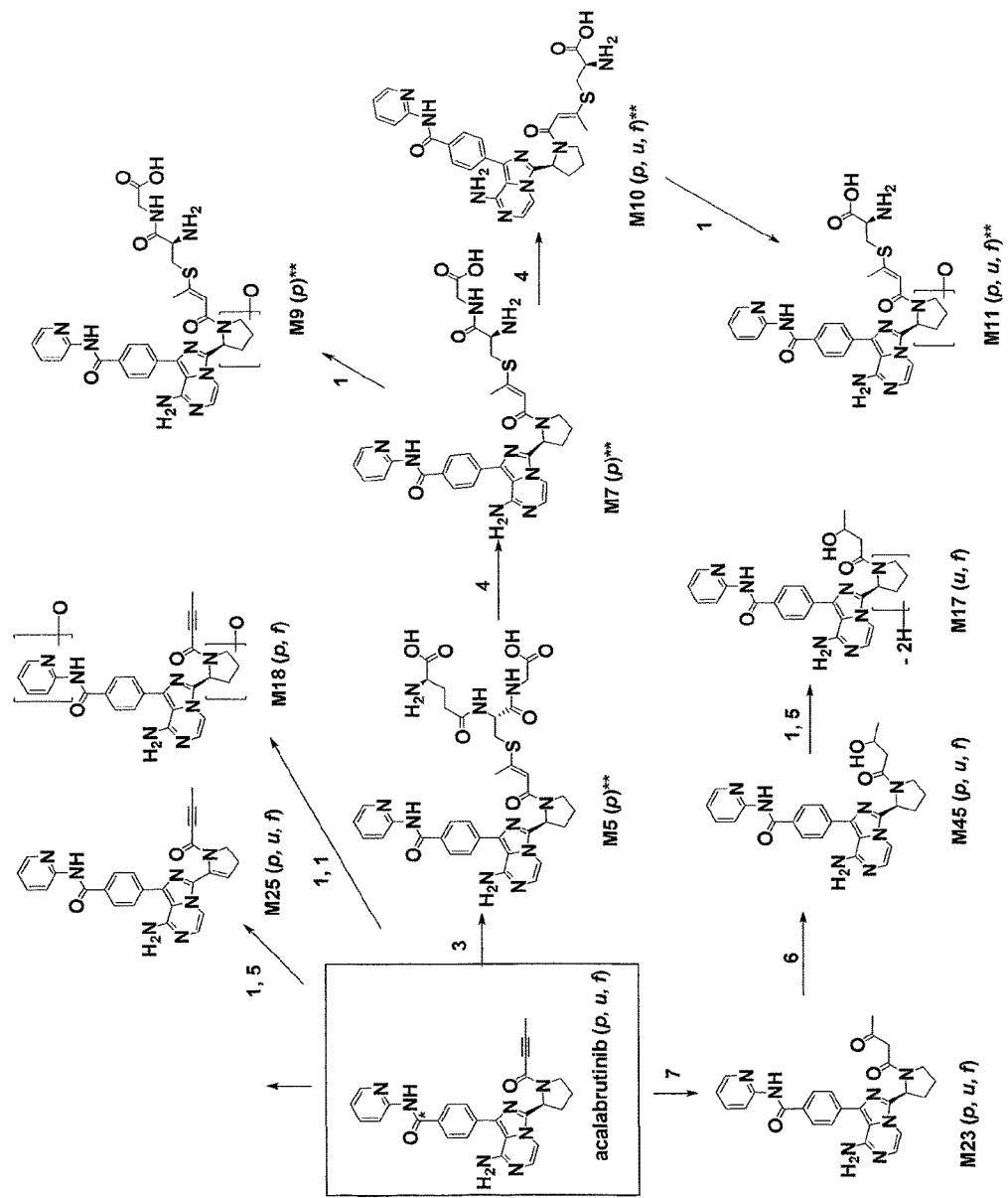
FIG. 8A and FIG. 8B together illustrate the biotransformation pathways of acalabrutinib in human.
Figure 8B:
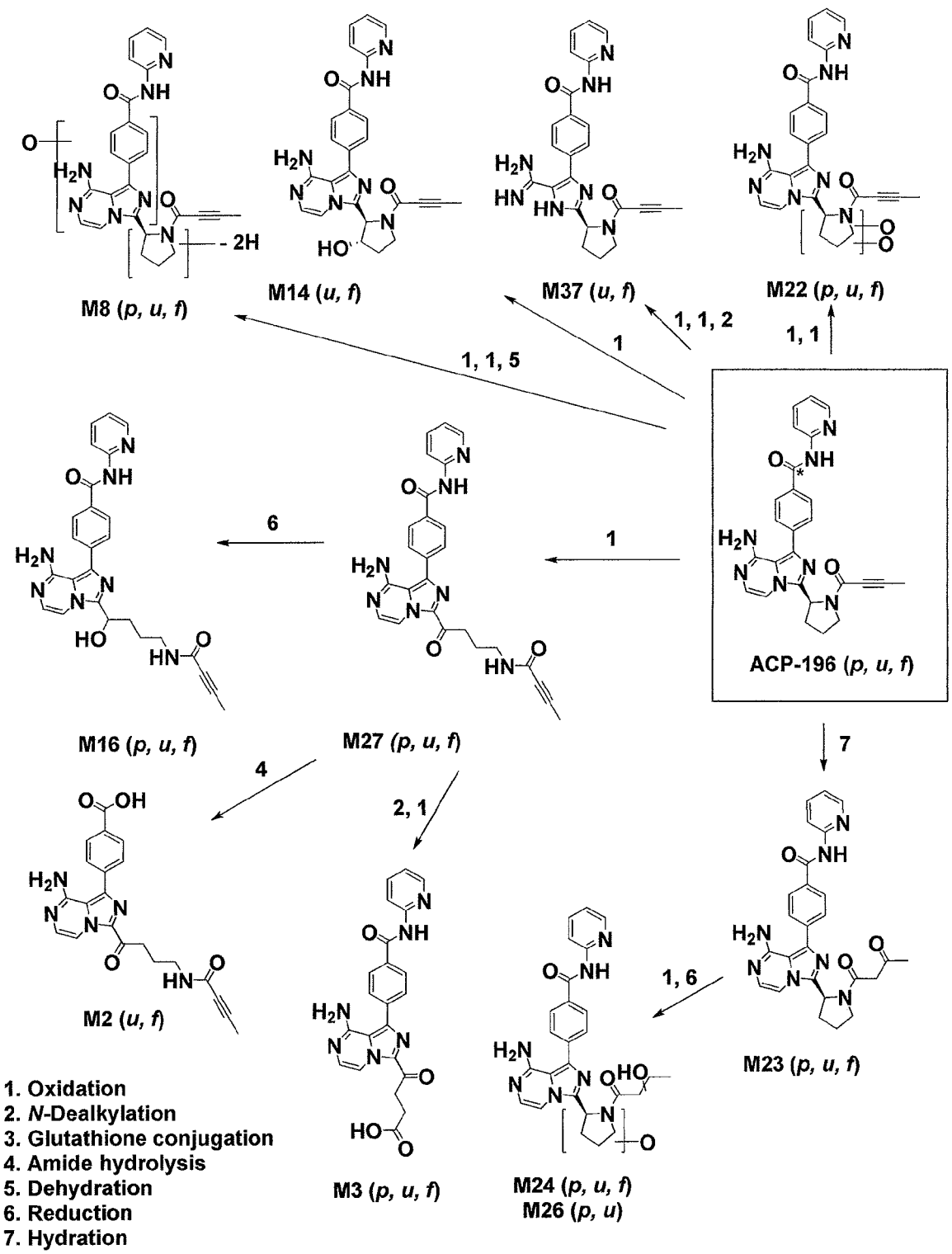

While the standard IMAP assay showed that metabolite M27 is a BTK inhibitor, further testing was required to determine whether M27 was a covalent inhibitor. M27 was tested in the BTK IMAP ATP competition assays with variable pre-incubation times (0, 30, and 60 minutes) and ATP concentrations (5, 25 and 100 µM). The results in Table 2 and FIG. 2 confirm that M27 is covalent inhibitors of BTK. Increasing the pre-incubation time resulted in a shift in potency for M27. Furthermore, there is loss of ATP competition following pre-incubation of BTK with M27, a result that is typical for compounds that bind covalently.

TABLE 2

| ATP, | $IC_{50}$ (nM) M27 | | |
|---|---|---|---|
| µM | 0 minute | 30 minutes | 60 minutes |
| 5 | 27.3 | 12.6 | 6.9 |
| 25 | 72.4 | 18.1 | 9.5 |
| 100 | 101.0 | 23.7 | 10.8 |

Example 6—BTK-WT and BTK-C481S LanthaScreen to Investigate Covalent Binding of Compounds Inhibitory activity on BTK wild type (BTK-WT) and BTK Cys481Ser mutant (BTK-C481S) was measured using the LanthaScreen assay technology from ThermoFisher according to manufacturer's protocol.

BTK-WT or BTK-C481 S (Genscript) were mixed and diluted with Eu-anti-GST antibody (Invitrogen) in Kinase buffer (50 mM Hepes pH 7.5+10 mM MgCl2+1 mM EGTA+0.01% Brij-35) to 15 and 6 nM, respectively. Final concentration in the assay for enzyme and antibody are 5 and 2 nM, respectively.

Tracer (Kinase Tracer 236, Invitrogen) is diluted in Kinase buffer to 90 nM. Final concentration in the assay is 30 nM.

Serial dilutions log 10 from 1 mM to 3.16 nM of test compounds are made in 100% DMSO. The dilutions in DMSO are then diluted 33-fold in Kinase buffer (50 mM Hepes pH 7.5+10 mM MgCl2+1 mM EGTA+0.01% Brij-35).

The assay is performed as follows: 5 µL/well of BTK-WT or BTK-C481S enzyme and EU-anti-GST antibody dilution is mixed with 5 µL/well tracer dilution and 5 µL/well of compound dilution in Kinase buffer. Final compound concentration in the assay ranged from 10 µM to 0.316 nM, with 1% DMSO final concentration in assay. Mixture was incubated at room temperature in the dark and at different times of incubation (5 min, 10 min, 20 min, 30 min, 40 min, 60 min, 90 min, 120 min, 180 min and 300 min) the TR-FRET signal was read at 615 nm and 665 nm. The ratio 665/615 was used to calculate values expressed as percentage of the difference in readout (S/N) of the controls with and without Tracer. IC50 values for each timepoint were determined by curve fitting of the experimental results in Dotmatics.

Figure 9:
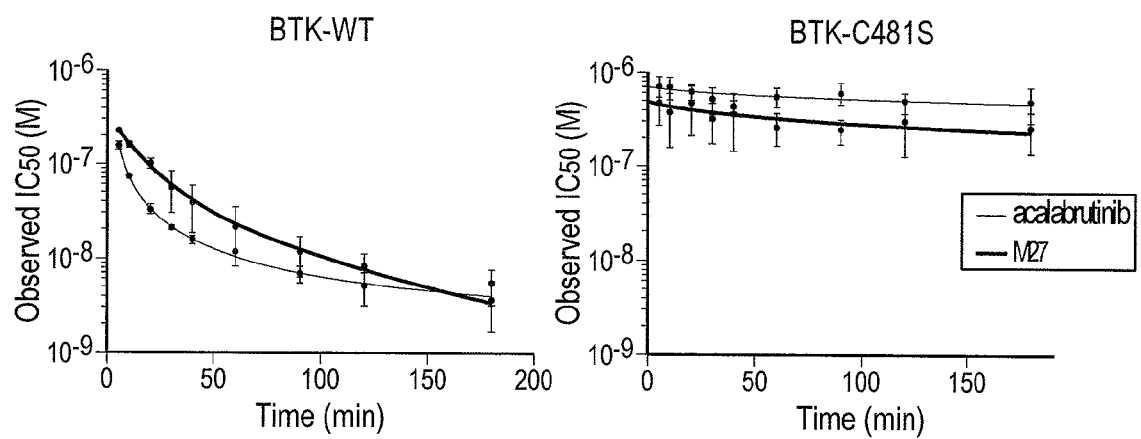
FIG. 9 illustrates acalabrutinib and M27 are covalent inhibitors of BTK. The left figure shows increase in potency over time for BTK-WT due to covalent binding over time. The right figure shows reversible binding (affinity) of compounds to BTK-C481S and does not change over time. Difference in potency between BTK-WT and BTK-C481S shows effect of covalent binding.

To confirm the covalent inhibition of M27, the inhibitory activity of M27 was investigated on BTK-WT and BTK Cys481Ser mutant (BTK C481 S), using the LanthaScreen assay technology from ThermoFisher according to the manufacturer's protocol. Measurements of IC50 were done at different timepoints following incubation of compounds with BTK and BTK-C481S. The results depicted in FIG. 9 confirm the covalent binding of M27 to BTK. The difference in potency between BTK-WT and BTK-C481S shows the effect of covalent binding of the compounds to BTK. The observed IC50 using BTK-C481 S reflects the reversible inhibition potency and does not change or hardly changes with time. The increase in potency observed with BTK-WT results from the capacity of M27 to bind covalently to C481 in the ATP pocket of BTK. The kinetics in covalent binding are determined by affinity of the compound to BTK and by the reactivity of the electrophile.

Using the data for M27 from the LanthaScreen assay on BTK-WT, the inhibition constants can be calculated for the parent and the metabolite. In order to determine the inhibition constants more accurately, the LanthaScreen experiments were repeated to include additional earlier timepoints following the start of the incubation. The results of these experiments are summarized in Table 3. The Ki and kinact parameters were derived from IC50 values over time, according to the method of Krippendorff et al (J Biomol Screen. 2009, 14(8):913-23) with measured Km=102 nM for the tracer used in the assay.

TABLE 3

| Compound | Ki (nM) | kinact (s$^{-1}$) | Kinact/Ki (s$^{-1}$ * M$^{-1}$)* |
|---|---|---|---|
| M27 | 188 ± 9 | 0.0031 ± 0.0003 | 1.65E+04 ± 7.77E+02 |

Example 7—BTK Target Occupancy in Ramos B Cells

Ramos B cells (ATCC, cat no. CRL-1923) were plated in 24-wells culture plates at 2×10$^6$ cells per well in a total volume of 900 µL DMEMF12+10% FBS+2 mM L-Glutamine+Pen/Strep. Allow the cells to rest 1 h at 5-7% CO2 and 37° C.

Serial dilutions log 10 from 10 mM to 316 nM of test compounds are made in 100% DMSO, followed by a 100-fold dilution into culture medium.

For each well, 100 µL was then transferred to well plate containing 900 µL of Ramos B cells. Final compound concentration range in the assay varied from 10 µM to 0.316 nM, with a final DMSO concentration of 0.1% and incubated at 5-7% CO$_2$ and 37° C. for 2h. Afterwards, cells are collected for the measurement of the BTK target occupancy using the BTK target occupancy ELISA as outlined below.

The percent of drug-bound BTK in Ramos B cell samples was determined by an ELISA based method as follows: OptiPlate 96-well plates (Perkin Elmer) were coated with 125 ng/well anti-BTK Ab (BD Biosciences) and blocked with BSA (Sigma-Aldrich). Samples containing Ramos B cells were lysed in ice cold lysis buffer containing 50 mM Tris-HCl pH 7.5, 250 mM sucrose, 5 mM MgCl2, 1 mM dithiothreitol (DTT), 0.05% digitonin, and protease inhibitor cocktail (Sigma-Aldrich). Cell lysates were then incubated for 1 h in the absence or presence of 1 µM acalabrutinib, a saturating concentration that results in complete BTK occupancy. Final amount of cell lysate used per well in BTK target occupancy ELISA is representative of 2×10$^5$ Ramos B cells. The difference with the signal of the cell lysates not incubated with an excess acalabrutinib represents free BTK (not occupied by a BTK inhibitor). Samples were incubated for 1 h with biotin tag compound of Formula (II) (100 nM). This probe will bind covalently to Cys481 in the ATP pocket in BTK when the ATP pocket is not occupied by a covalent BTK inhibitor. Each sample was then added in duplicate to the prepared Optiplate and incubated for 2h at ambient temperature. Plates were washed with PBS+0.05% Tween20 four times. Streptavidin-HRP (Invitrogen; ELISA grade) was added at 100 µL/well (120 ng/mL) and incubated for 1 hour at room temperature. Plates were washed with PBS+ 0.05% Tween20 three times and then washed with PBS (without Tween 20) two times. One hundred L/well of SuperSignal ELISA Femto Substrate (ThermoFisher Scientific) was added and then chemiluminescence was measured after 1 minute (EnVision® plate reader; PerkinElmer). The percent of BTK occupancy for each sample was calculated relative to the vehicle control. The signal from the vehicle control without exogenous acalabrutinib represents 100% free BTK (or 0% occupied BTK), whereas the signal from the vehicle control with exogenous acalabrutinib represents 0% free BTK (or 100% occupied BTK). The incubation of each cell lysate with 1 µM acalabrutinib was used to correct for background signal not related to free BTK:

% Free BTK sample X=(Sample X−Sample X+drug[1 uM])/(Day 1 Predose−Day 1 Predose+drug[1 uM])×100%

% Occupied BTK=100%−% Free BTK

Figure 10:
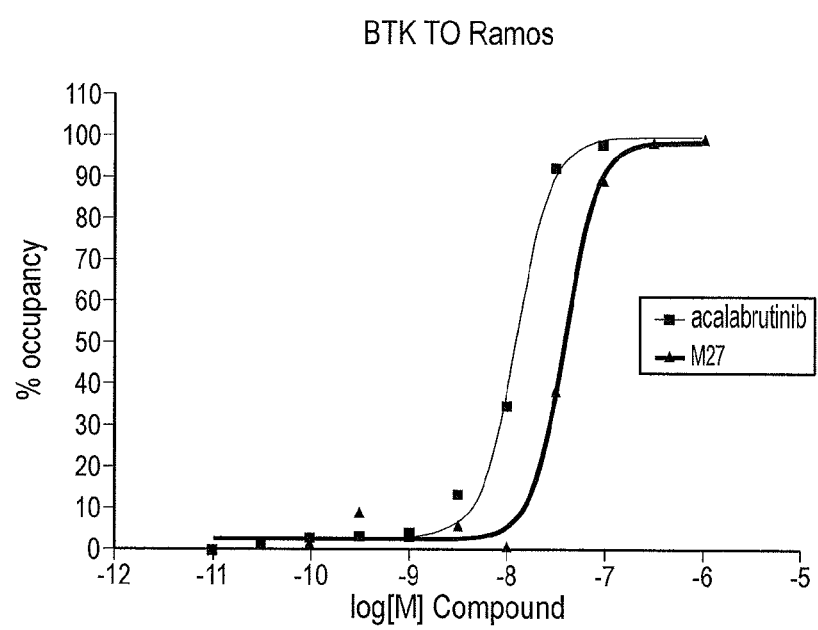
FIG. 10 illustrates BTK target occupancy (BTK TO) of acalabrutinib and M27 in Ramos cells.
Figure 11:
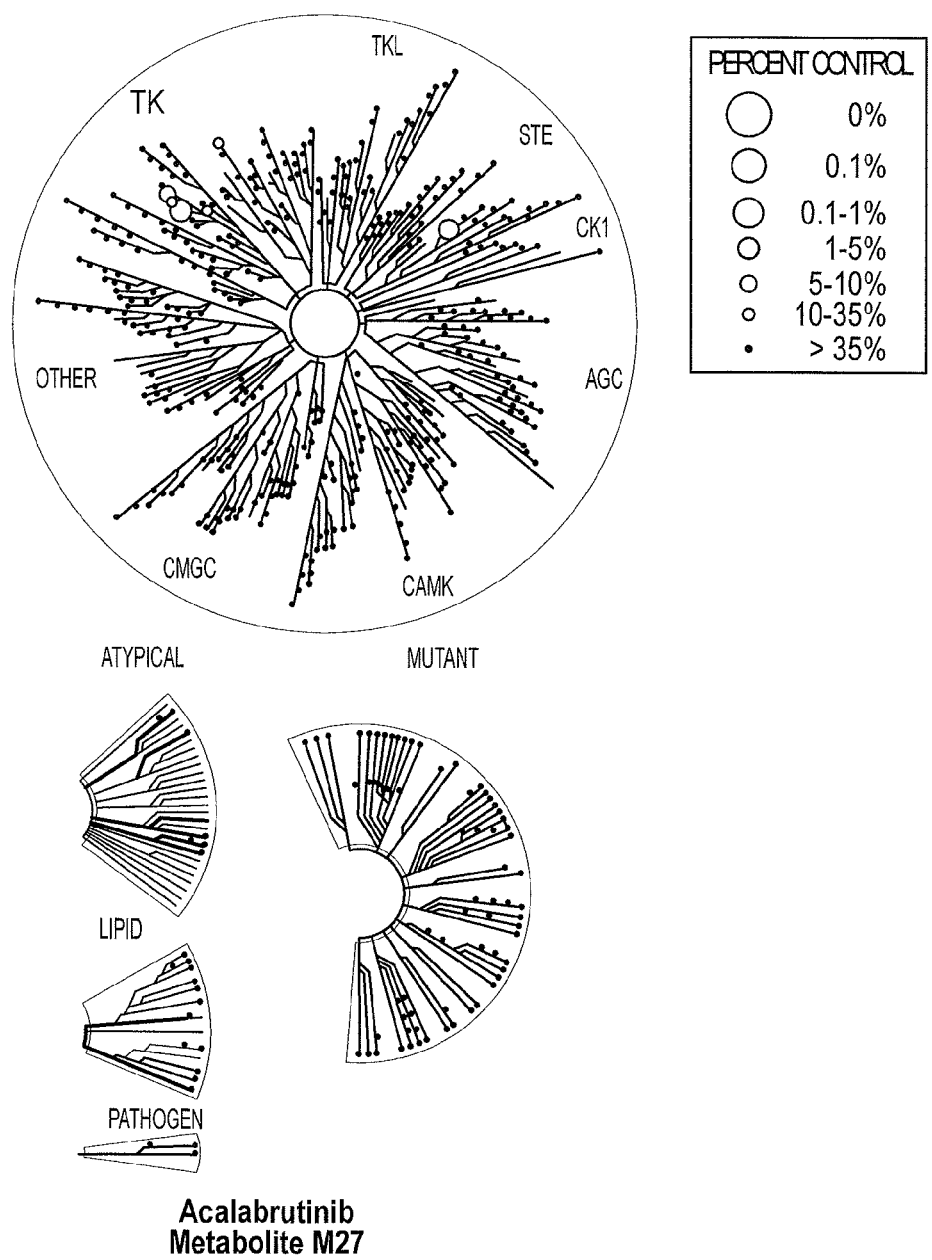
FIG. 11 illustrates KINOMEscan profiling at a single dose (1 µM) of M27 (DiscoveRx scanMAX).
Figure 12:
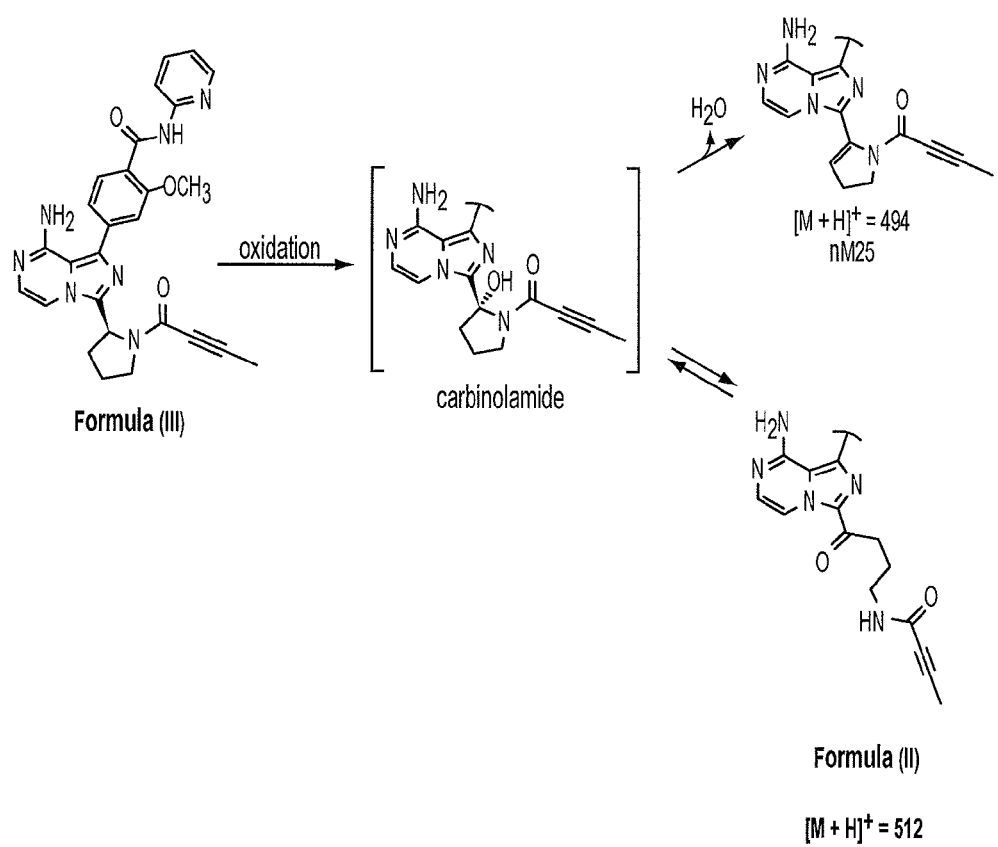
FIG. 12 illustrates the metabolic pathways to the compound of Formula (II) from Formula (III).

The binding of M27 to BTK in cells was performed using the Ramos (Burkitt's lymphoma) cell line. Ramos cells were incubated with a dose range of M27 and BTK target occupancy was determined by ELISA. Results are shown in FIG. 10 and Table 4. These data also confirm that M27 bind covalently to BTK in Ramos cells, as given the set up of the BTK target occupancy ELISA, a reversible inhibitor would be washed off during the assay.

TABLE 4

| Parameter | M27 IC$_{50}$ (nM) |
|---|---|
| BTK target occupancy | 39 |

Example 8—Human Peripheral Blood Mononuclear Cell (PBMC) CD69 Assay and in WB Assay Whole blood was collected in heparin-coated Vacutainer tubes (BD Biosciences, San Jose, Calif.) and used for isolation of PBMCs using Ficoll-Hypaque (Pharmacia, Uppsala, Sweden). Isolated PBMCs were cryopreserved in 90% FCS/10% DMSO until later use.

Cells from cryogenic storage were thawed in a 37° C. water bath, diluted with RPMI/1% FCS, washed 2 times, and then plated at 2×10$^5$ cells per well in RPMI/10% FCS in 96 well plates.

Serial dilutions log 100 from 10 mM to 316 nM of test compounds are made in 100% DMSO, followed by a 100-fold dilution into RPMI/1% FCS. For each well, 10 μL was then transferred to the deep well plate containing 90 μL of PBMC cells. Final compound concentration range in the assay ranged from 10 μM to 0.316 nM, with a final DMSO concentration of 0.1%. PBMCs are then incubated for 2 h at 37° C. in presence or absence of test compounds, prior to stimulation with goat F(ab')2 anti-IgM (Southern Biotech, #2022-14, final concentration in assay 5 μg/mL) for 18 hours.

Following stimulation with anti-IgM, PBMCs were incubated on ice for 30 min with anti-CD69-FITC, anti-CD19-BV421 (BD Biosciences #555530 and #562440, respectively) and 7AAD (Life Technologies # A1310). Flow cytometry was performed and fluorescence values were obtained from the CD69-FITC channel in CD19+ gated life B cells. EC50 values are determined by curve fitting of the experimental results using GraphPad Prism.

PBMC assay: Cryopreserved PBMC were thawed, washed, and suspended at 2×105 cells/well in RPMI+10% FBS in 96-well plates. Test compounds were added using a ½ log dose titration (final concentration was 10 μM to 0.316 nM) and incubated for 2h incubation at 37° C., 5% C02. Final DMSO concentration in the assay was 0.1%. For the washout part of the experiment, PBMCs were spun down and the cell pellet resuspended in culture medium without test compound. This was repeated twice. To the PBMCs with and without washout, goat anti-human IgM F(ab')2 antibody (Southern Biotech) was added (final concentration 5 μg/mL) and the cells were incubated for a further 18 h. Cells were then stained with CD69-FITC and CD19-BV421 antibodies (BD Biosciences) for 30 minutes at 4° C. After washing off unbound antibody, 7-AAD was added as a viability measure, followed by flow cytometry using a FACSVerse instrument (BD Biosciences). The percentage of CD69-positive cells was obtained from the CD 19+B lymphocyte gate using FCSExpress analysis software (De Novo Software). EC50 values were determined by curve fitting of the experimental results using Dotmatics.

WB assay: Forty-five μL blood was diluted 1:1 in RPMI+ 1% FBS and incubated with test compound, as described above. Blood cells were stimulated with 10 μg/mL mouse anti-human anti-IgD antibody (BD Biosciences, final concentration in assay 10 μg/mL) and incubated for 18h. Cells were stained with CD69-FITC, CD86-PE, and CD19-BV421 (BD Biosciences) for 15 minutes at room temperature, followed by RBCs lysis with FACS Lysing Solution (BD Biosciences). Cells were washed 3 times with 1 mL/well PBS+0.5% BSA, followed by flow cytometric analyses. Median fluorescence intensity values for CD69 were obtained from the CD19+B lymphocyte gate using FCSExpress analyses software (De Novo Software). EC50 values were determined by curve fitting of the experimental results using Dotmatics.

The potency of BTK inhibitors in primary B cells can be assessed in assays that evaluate functional changes after BCR-activation in the presence of inhibitor. Inhibition of specific phosphorylated epitopes on signaling proteins and more distal measures of BCR activation such as increased expression of CD86 (B7-2) and CD69 on the cell surface can be measured by flow cytometry (see Report R2013003A). In this study, effects of M27 on CD69 expression were assessed. Results of CD69 up-regulation in human PBMC preparations and WB are summarized in Table 5.

TABLE 5

| Assay | M27 $EC_{50}$ (nM) | Formula (II) $EC_{50}$ (nM) |
|---|---|---|
| hPBMC: anti-IgM-induced CD69 | 26 ± 16 | 19 ± 6 |
| hWB: anti-IgD-induced CD69 | 64 ± 6 | 137 ± 36 |

The data (Tables 5) confirm the findings that M27 is covalent inhibitors of BTK, and M27 covalently binds to and fully occupies BTK in Ramos B cells.

Example 9: Kinome Profiling of M27

Kinase profiling was performed with M27 was done at DiscoveRx at a single dose of 1 μM on all available kinases (KINOMEscan). The overall kinase selectivity score is in Table 6. Results show an overall kinase selectivity profile for M27 at 1 μM. Kinases inhibited >65% at 1 μM for M27 were followed up with a dose response at DiscoveRx. The Kd values determined from this experiment are listed in Table 7. The M27 had IC50 values <1 μM for almost the same set of kinases with exception of TXK, but with additional inhibition of BRK (PTK6).

TABLE 6

Selectivity score results from KINOMEscan (DiscoveRx scanMAX) profiling for M27

| Kinase | Selectivity Score M27 |
|---|---|
| S(35) | 0.013 |
| S(10) | 0.005 |
| S(1) | 0 |

TABLE 7

Kd values of kinases with >65% inhibition at 1 μM for M27 (NT = not tested)

| Kinase | Kd (nM) M27 |
|---|---|
| BTK | 29 |
| BMX | 190 |
| BRK (PTK6) | 150 |
| ERBB2 | 120 |
| ERBB4 | 970 |
| LIMK1 | 400 |
| MEK5 | 69 |
| TEC | 40 |
| TXK | 1100 |

We claim:

1. A pharmaceutical composition comprising a compound of Formula (I) or Formula (II) having the structure:

(I)

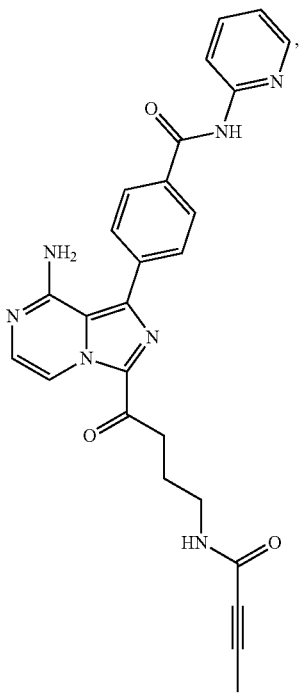

(II)

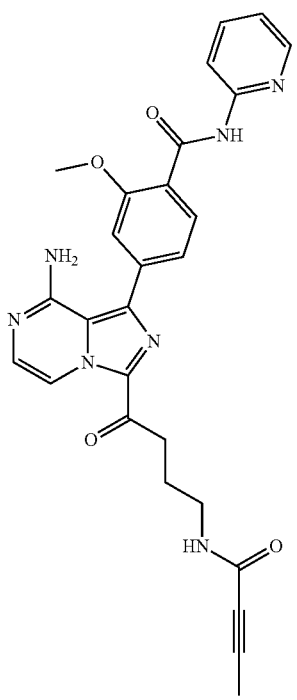

or a pharmaceutically acceptable salt thereof and at least one pharmaceutically acceptable excipient.

2. A method of treating a B cell hematological malignancy in a patient in need thereof comprising the step of administering a therapeutically effective amount of the pharmaceutical composition of claim 1 to the patient wherein the B cell hematological malignancy is selected from the group consisting of chronic lymphocytic leukemia, small lymphocytic leukemia and mantle cell lymphoma.

3. The method of claim 2, wherein the B cell hematological malignancy is small lymphocytic leukemia.

4. The method of claim 2, wherein the B cell hematological malignancy is chronic lymphocytic leukemia.

5. A method of claim 2, wherein the B cell hematological malignancy is mantle cell lymphoma.

6. The method of claim 2, wherein the pharmaceutical composition is administered orally.

7. The pharmaceutical composition of claim 1, comprising a compound of Formula (I).

8. A method of treating chronic lymphocytic leukemia in a patient in need thereof comprising the step of administering a therapeutically effective amount of the pharmaceutical composition of claim 7 to the patient.

9. A method of treating small lymphocytic leukemia in a patient in need thereof comprising the step of administering a therapeutically effective amount of the pharmaceutical composition of claim 7 to the patient.

10. A method of treating mantle cell lymphoma in a patient in need thereof comprising the step of administering a therapeutically effective amount of the pharmaceutical composition of claim 7 to the patient.

11. The pharmaceutical composition of claim 1, comprising a compound of Formula (II).

12. A method of treating chronic lymphocytic leukemia in a patient in need thereof comprising the step of administering a therapeutically effective amount of the pharmaceutical composition of claim 11 to the patient.

13. A method of treating small lymphocytic leukemia in a patient in need thereof comprising the step of administering a therapeutically effective amount of the pharmaceutical composition of claim 11 to the patient.

14. A method of treating mantle cell lymphoma in a patient in need thereof comprising the step of administering a therapeutically effective amount of the pharmaceutical composition of claim 11 to the patient.

* * * * *